US006825029B2

United States Patent
Dunican et al.

(10) Patent No.: US 6,825,029 B2
(45) Date of Patent: Nov. 30, 2004

(54) NUCLETOIDE SEQUENCES WHICH CODE FOR THE OPCA GENE

(75) Inventors: Laurence K. Dunican, deceased, late of County Galway (IE); by Rita Dunican, legal representative, Galway (IE); Ashling McCormack, County Westmeath (IE); Cliona Stapelton, County Tipparary (IE); Kevin Burke, County Galway (IE); Bernd Moritz, Niederzier (DE); Lothar Eggeling, Jülich (DE); Hermann Sahm, Jülich (DE); Bettina Möckel, Bielefeld (DE); Anke Weissenborn, Tübingen (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 10/137,655

(22) Filed: May 3, 2002

(65) Prior Publication Data

US 2003/0138917 A1 Jul. 24, 2003

Related U.S. Application Data

(63) Continuation-in-part of application No. 09/531,267, filed on Mar. 20, 2000, now abandoned.
(60) Provisional application No. 60/142,915, filed on Jul. 9, 1999.

(51) Int. Cl.$^7$ .......................... C12N 9/04; C12N 15/00; C12N 01/20; C12Q 1/32; C07K 17/00
(52) U.S. Cl. ................. 435/252.32; 435/26; 435/320.1; 435/325; 435/252.3; 435/190; 536/23.2; 530/350
(58) Field of Search ....................... 435/26, 190, 320.1, 435/325, 252.3, 252.32; 536/23.2; 530/350

(56) References Cited

FOREIGN PATENT DOCUMENTS

| EP | 1 108 790 | 6/2001 |
|---|---|---|
| JP | 9224 661 | 9/1997 |
| WO | WO 01/00844 | 1/2001 |

OTHER PUBLICATIONS

Bork, Genome Research, 10:398–400, 2000.*
Seffernick et al., J. Bacteriol. 183(8):2405–2410, 2001.*
Witkowski et al., Biochemistry 38:11643–11650, 1999.*
EMBL:E13655, Hatakeyama et al., "gDNA encoding glucose–6–phosphate dehydrogenase," XP002152311, 1998.
Kobayashi, et al., "Purification and Properties of NAD–Dependent D–Glucose Dehydrogenase Produced by Alkalophilic Corynebacterium sp. No. 93–1," Agricultural and Biological Chemistry, vol. 44, No. 10, 1980, pp. 2261–2269.

ENBKLSO33285, Newman, J. et al., "Synechococcus PCC7942 zwf region, fructose 1,6–biophosphatase (fbp), glucose 6–phosphate dehydrogenase (zwf), OpcA (opcA), cytochrome b6 (petD), and cytochrome b6f complex subunit IV (petB) genes, complete cds," FEMS Microbiology Letters, vol. 133, No. 1–2, 1995, pp. 187–193, XP000967662.

Summers et al., "Transcriptional regulator of zwf, encoding glucose–6–phosphate dehydrogenase, from the cyanobacterium Nostoc punctiforme strain ATCC 29133," Molecular Microbiology, vol. 22, No. 3, 1996, pp. 473–480.

Sequence Alignment, GeneSeq. Accession No. AAT88030, Dec. 1997.

Sequence Alignment, SwissProt. Accession No. POR–AVESA, Apr. 1990.

Broun et al., Science 282: 1315–1317, 1998.

Smith et al., Nature Biotechnology 15: 1222–1223, 1997.

Van de Loo et al, Proc. Natl. Acad. Sci. 92: 6743–6747, 1995.

Brenner, TIG 15: 132–1333, 1999.

Hagen, K. D. and J. C. Meeks (2001). "The unique cyanobacterial protein OpcA is an allosteric effector of glucose–6–phosphate dehydrogenase in Nostoc punctiforme ATCC 29133." *J Biol Chem* 276(15): 11477–86.

Moritz, B., K. Striegel, et al. (2000). "Kinetic properties of the glucose–6–phosphate and 6–phosphogluconate dehydrogenases from Corynebacterium glutamicum and their application for predicting pentose phosphate pathway flux in vivo." *Eur J Biochem* 267(12): 3442–52.

Schaeffer, F. and R. Y. Stanler (1978). "Glucose–6–phosphate dehydrogenase of Anabaena sp. Kinetic and molecular properties." *Arch Microbiol* 116(1): 9–19.

Sundaram, S., H. Karakaya, et al. (1998). "Multiple oligomeric forms of glucose–6–phosphate dehydrogenase in cyanobacteria and the role of OpcA in the assembly process." *Microbiology* 144 (Pt 6): 1549–56.

Summers, M. L. and J. C. Meeks (1996). "Transcriptional regulation of zwf, encoding glucose–6–phosphate dehydrogenase, from the cyanobacterium Nostoc punctiforme strain ATCC 29133." *Mol Microbiol* 22(3): 473–80.

* cited by examiner

*Primary Examiner*—Rebecca E. Prouty
*Assistant Examiner*—Delia M. Ramirez
(74) *Attorney, Agent, or Firm*—Pillsbury Winthrop LLP

(57) ABSTRACT

The present invention relates to polynucleotides that encode proteins having OpcA enzymatic activity. These polynucleotides can be used for increasing lysine biosynthesis in *Coryneform glutamicum*.

17 Claims, 3 Drawing Sheets

NUCLETOIDE SEQUENCES WHICH CODE FOR THE OPCA GENE

CROSS REFERENCE TO RELATED APPLICATION

The present application is a continuation-in-part of U.S. application Ser. No. 09/531,267 filed on Mar. 20, 2000 now abandoned, which, in turn, claims the benefit of U.S. Provisional Application No. 60/142,915 filed on Jul. 9, 1999. The contents of U.S. application Ser. No. 09/531,267 are incorporated herein by reference in their entirety.

FIELD OF THE INVENTION

The invention provides nucleotide sequences which code for the opcA gene and a process for the fermentative preparation of amino acids, in particular L-lysine using coryneform bacteria in which the opcA gene is amplified.

DESCRIPTION OF BACKGROUND ART

Amino acids, in particular L-lysine, are used in human medicine and in the pharmaceuticals industry, but in particular in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the processes can relate to fermentation measures, such as e.g. stirring and supply of oxygen, or the composition of the nutrient media, such as e.g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the lysine analogue S-(2-aminoethyl)-cysteine, or are auxotrophic for metabolites of regulatory importance and produce L-amino acids, such as e.g. L-lysine, are obtained in this manner. Methods of the recombinant DNA technique have also been employed for some years for improving the strain of Corynebacterium strains which produce amino acids.

The importance of the pentose phosphate cycle for the biosynthesis is known.

Thus Oishi and Aida (Agricultural and Biological Chemistry 29, 83–89 (1965)) already report on the "hexose monophosphate shunt" of *Brevibacterium ammoniagenes*. Sugimoto and Shio (Agricultural and Biological Chemistry 51, 101–108 (1987)) report on the regulation of glucose 6-phosphate dehydrogenase in *Brevibacterium flavum*. Sugimoto and Shio (Agricultural and Biological Chemistry 51, 1257–11263 (1987)) report on the regulation of glucose 6-phosphate dehydrogenase in *Brevibacterium flavum*.

JP-A-09224661 discloses the nucleotide sequence of the glucose 6-phosphate dehydrogenase gene, called zwf, of *Brevibacterium flavum* MJ-223 (FERM BP-1497). JP-A-09224661 describes the N-terminal amino acid sequence of the Zwf polypeptide as Met Val Ile Phe Gly Val Thr Gly Asp Leu Ala Arg Lys Lys Leu (SEQ ID NO: 24).

However, it has not been possible to confirm this.

SUMMARY OF THE INVENTION

Amino acids, in particular L-lysine, are used in human medicine, in the pharmaceuticals industry and in particular in animal nutrition. There is therefore a general interest in providing new improved processes for the preparation of amino acids, in particular L-lysine.

When L-lysine or lysine are mentioned in the following, not only the base but also the salts, such as e.g. lysine monohydrochloride or lysine sulfate, are also meant by this.

The invention provides an isolated polynucleotide from coryneform bacteria, comprising at least one polynucleotide sequence chosen from the group consisting of a) polynucleotide which is identical to the extent of at least 70% to a polynucleotide which codes for polypeptides which comprise at least one of the amino acid sequences according to SEQ ID No. 3 or SEQ ID No. 5 or SEQ ID No. 8 or SEQ ID No. 10, b) polynucleotide which codes for polypeptides which comprise amino acid sequences which are identical to the extent of at least 70% to the amino acid sequences according to SEQ ID No. 3 or SEQ ID No. 5 or according to SEQ ID No. 8 or SEQ ID No. 10, c) polynucleotide which is complementary to the polynucleotides of a) or b), or d) polynucleotide comprising at least 15 successive nucleotides of the polynucleotide sequences of a), b) or c).

The invention also provides the polynucleotide as described above, this polynucleotide preferably being a DNA which is capable of replication, comprising:

(i) one or more nucleotide sequence(s) chosen from the group consisting of SEQ ID No. 1, SEQ ID No. 4, SEQ ID No. 6, SEQ ID No. 9, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide comprising the nucleotide sequence as shown in SEQ ID No. 4 or SEQ ID No. 9, a polynucleotide which codes for a polypeptide which comprises at least one of the amino acid sequences as shown in SEQ ID No. 3, SEQ ID No. 5, SEQ ID No. 8 or SEQ ID No. 10, a vector containing the above polynucleotide, and coryneform bacteria, serving as the host cell, which contain the vector.

The invention also provides polynucleotides which substantially comprise a polynucleotide sequence, which are obtainable by screening by means of hybridization of a corresponding gene library, which comprises the complete gene with the polynucleotide sequence corresponding to SEQ ID No. 4 or SEQ ID No. 9, with a probe which comprises the sequence of the polynucleotide mentioned, according to SEQ ID No. 4 or SEQ ID No. 9 or a fragment thereof, and isolation of the DNA sequence mentioned.

BRIEF DESCRIPTION OF THE SEQUENCES

SEQ ID No. 1: DNA sequence isolated from *Corynebacterium glutamicum* ATCC13032.

SEQ ID No. 2: Amino acid sequence of the Zwf protein derived from SEQ ID No. 1.

SEQ ID No. 3: Amino acid sequence of the OpcA protein derived from SEQ ID No. 1.

SEQ ID No. 4: DNA sequence of the opcA gene of ATCC13032 taken from SEQ ID No. 1.

SEQ ID No. 5: Amino acid sequence of the OpcA protein derived from SEQ ID No. 4.

SEQ ID No. 6: DNA sequence isolated from *Corynebacterium glutamicum* ASO19.

SEQ ID No. 7: Amino acid sequence of the Zwf protein derived from SEQ ID No. 6.

SEQ ID No. 8: Amino acid sequence of the OpcA protein derived from SEQ ID No. 6.

SEQ ID No. 9: DNA sequence of the opcA gene of ASO19 taken from SEQ ID No. 6.

SEQ ID No. 10: Amino acid sequence of the OpcA protein derived from SEQ ID No. 9.

SEQ ID No. 11: Amino acid sequence of the N-terminus of the Zwf protein of the glucose 6-phosphate dehydrogenase from ATCC13032 which can be isolated.

SEQ ID No. 12: Amino acid sequence of the N-terminus of the OpcA protein of the glucose 6-phosphate dehydrogenase, which can be isolated from ATCC13032.

BRIEF DESCRIPTION OF THE FIGURES

Embodiments of the invention will be described with reference to the following Figures, in which the base pair numbers stated are approximate values obtained in the context of reproducibility, and in which.

DETAILED DESCRIPTION

Figure 1:
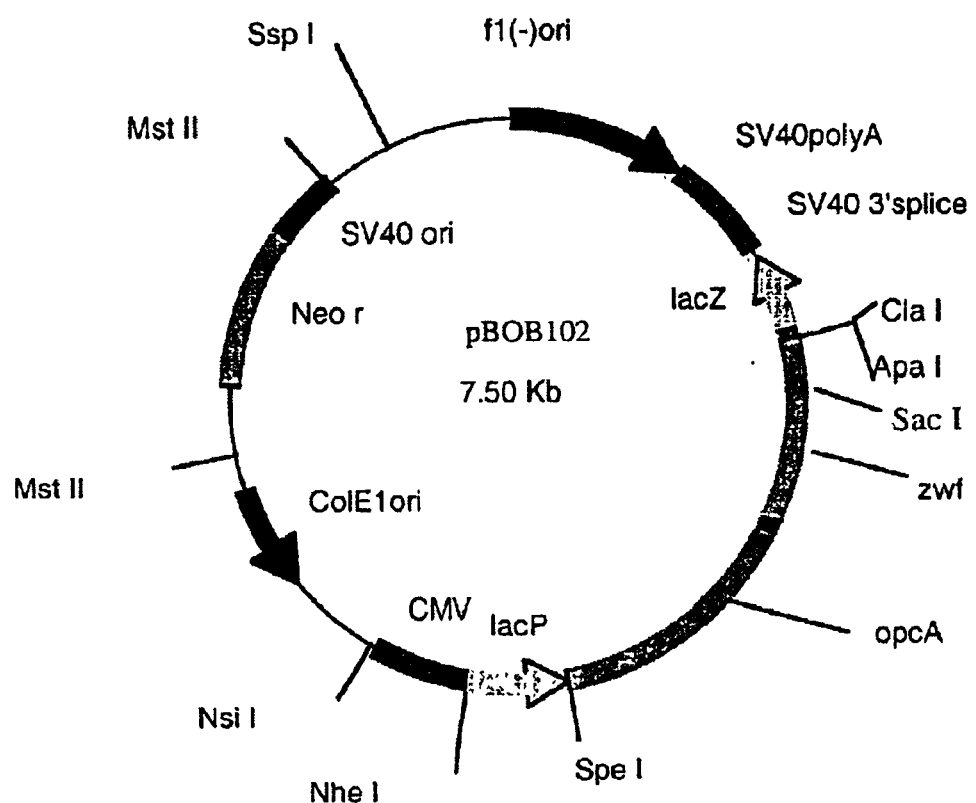
FIG. 1 is a map of the plasmid pBOB102.

Polynucleotide sequences according to the invention are suitable as hybridization probes for RNA, cDNA and DNA, in order to isolate, in the full length, cDNA which code for OpcA protein and to isolate those cDNA or genes which have a high similarity of sequence with that of the opcA gene.

Polynucleotide sequences according to the invention are furthermore suitable as primers for the preparation of DNA of genes which code for OpcA protein by the polymerase chain reaction (PCR).

Such oligonucleotides which serve as probes or primers comprise at least 30, preferably at least 20, especially preferably at lease 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include a polypeptide according to SEQ ID No. 3, SEQ ID No. 5, SEQ ID No. 8 or SEQ ID No. 10, in particular those with the biological activity of the OpcA gene product, and also those which are identical to the extent of at least 70% to the polypeptide according to SEQ ID No. 3, SEQ ID No. 5, SEQ ID No. 8 or SEQ ID No. 10, and preferably are identical to the extent of at least 80% and in particular to the extent of at least 90% to 95% to the polypeptide according to SEQ ID No. 3, SEQ ID No. 5, SEQ ID No. 8 or SEQ ID No. 10, and have the activity mentioned.

The invention also provides the new Zwf protein which forms the Zwf sub-unit of glucose 6-phosphate dehydrogenase. The amino acid sequence of the translation product is shown in SEQ ID no. 2 and SEQ ID No. 7. The N-terminal amino acid sequence of the Zwf sub-unit, which can be isolated, of glucose 6-phosphate dehydrogenase is shown in SEQ ID No. 11.

The invention also provides a process for the fermentative preparation of amino acids, in particular L-lysine, using coryneform bacteria which in particular already produce an amino acid, and in which the nucleotide sequences which code for the opcA gene are amplified, in particular over-expressed, optionally together with the zwf gene.

The term "amplification" in this connection describes the increase in the intracellular activity of one or more enzymes or proteins in a microorganism which are coded by the corresponding DNA, for example by increasing the number of copies of the gene or genes, using a potent promoter or using a gene or allele which codes for a corresponding enzyme or protein having a high activity, and optionally combining these measures.

By amplification measures, in particular over-expression, the activity or concentration of the corresponding enzyme or protein is in general increased by at least 10%, 25%, 50%, 75%, 100%, 150%, 200%, 300%, 400% or 500%, up to a maximum of 1000% or 2000%, based on that of the wild-type enzyme or protein or the activity or concentration of the enzyme or protein in the starting microorganism.

The microorganisms which the present invention provides can prepare L-amino acids, in particular L-lysine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum*, are, for example, the known wild-type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Corynebacterium melassecola* ATCC17965

*Brevibacterium flavum* ATCC14067

*Brevibacterium lactofermentum* ATCC13869 and

*Brevibacterium divaricatum* ATCC14020 and L-lysine-producing mutants or strains prepared therefrom, such as, for example

*Corynebacterium glutamicum* FERM-P 1709

*Brevibacterium flavum* FERM-P 1708

*Brevibacterium lactofermentum* FERM-P 1712

*Corynebacterium glutamicum* FERM-P 6463

*Corynebacterium glutamicum* FERM-P 6464 and

*Corynebacterium glutamicum* DSM5715

*Corynebacterium glutamicum* DM58-1

*Corynebacterium glutamicum* DSM12866 and L-threonine-producing mutants or strains prepared therefrom, such as, for example

*Corynebacterium glutamicum* ATCC21649

*Brevibacterium flavum* BB69

*Brevibacterium flavum* DSM5399

*Brevibacterium lactofermentum* FERM-BP 269

*Brevibacterium lactofermentum* TBB-10 and L-isoleucine-producing mutants or strains prepared therefrom, such as, for example

*Corynebacterium glutamicum* ATCC 14309
*Corynebacterium glutamicum* ATCC 14310
*Corynebacterium glutamicum* ATCC 14311
*Corynebacterium glutamicum* ATCC 15168
*Corynebacterium ammoniagenes* ATCC 6871 and L-tryptophan-producing mutants or strains prepared therefrom, such as, for example

*Corynebacterium glutamicum* ATCC21850 and
*Corynebacterium glutamicum* KY9218(pKW9901).

The inventors have succeeded in isolating the new opcA gene of *C. glutamicum* which codes for the OpcA sub-unit of the enzyme glucose 6-phosphate dehydrogenase (EC 2.7.1.11).

To isolate the opcA gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) or the handbook by Sambrook et al.: Molecular Cloning, A Laboratory Manual (Cold Spring Harbor Laboratory Press, 1989) may be mentioned as an example. A very well-known gene library is that of the *E. coli* K-12 strain W3110 set up in λ vectors by Kobara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Bormann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)). O'Donohue (The Cloning and Molecular Analysis of Four Common Aromatic Amino Acid Biosynthetic Genes from *Corynebacterium glutamicum*. Ph.D. Thesis, National University of Ireland, Galway, 1997) describes the cloning of *C. glutamicum* genes using the λ Zap expression system described by Short et al. (Nucleic Acids Research, 16: 7583).

To prepare a gene library of *Corynebacterium glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can then in turn be subcloned and subsequently sequenced in the usual vectors which are suitable for sequencing, such as is described e.g. by Sanger et al. (Proceedings of the National Academy of Sciences of the United States of America, 74:5463–5467, 1977).

The DNA sequences obtained can then be investigated with known algorithms or sequence analysis programs, such as e.g. that of Staden (Nucleic Acids Research 14, 217–232 (1986)), the GCG program of Butler (Methods of Biochemical Analysis 39, 74–97 (1998)) the FASTA algorithm of Pearson and Lipman (Proceedings of the National Academy of Sciences USA 85,2444–2448 (1988)) or the BLAST algorithm of Altschul et al. (Nature Genetics 6, 119–129 (1994)) and compared with the sequence entries which exist in databanks accessible to the public. Databanks for nucleotide sequences which are accessible to the public are, for example, that of the European Molecular Biology Laboratories (EMBL, Heidelberg, Germany) or that of the National Center for Biotechnology Information (NCBI, Bethesda, Md., USA).

The invention provides a new DNA sequence of *Corynebacterium glutamicum* which codes for the opcA gene and which is a constituent of the present invention as SEQ ID NO 1 and SEQ ID NO 4. The amino acid sequence of the corresponding protein has furthermore been derived from the present DNA sequence by the methods described above. The resulting amino acid sequence of the OpcA gene product is shown in SEQ ID NO 3 and SEQ ID NO 5. The molecular weight resulting from the amino acid sequence of the OpcA gene product is approx. 34.7 kilo Dalton (kDa).

SEQ ID NO 1 also shows the coding region of the zwf gene. The resulting amino acid sequence of the Zwf gene product is shown in SEQ ID NO 2. The molecular weight resulting from the amino acid sequence of the Zwf gene product is approx. 57.5 kilo Dalton.

A gene library produced in the manner described above can furthermore be investigated by hybridization with nucleotide probes of known sequence, such as, for example, the zwf gene (JP-A-09224661). The cloned DNA of the clones which show a positive reaction in the hybridization is sequenced in turn to give on the one hand the known nucleotide sequence of the probe employed and on the other hand the adjacent new DNA sequences.

The invention also provides a new DNA sequence of *Corynebacterium glutamicum* which codes for the opcA gene and which is a constituent of the present invention as SEQ ID NO 6 and SEQ ID NO 9. The amino acid sequence of the corresponding protein has furthermore been derived from the present DNA sequence by the methods described above. The resulting amino acid sequence of the OpcA gene product is shown in SEQ ID NO 8 and SEQ ID NO 10. The molecular weight resulting from the amino acid sequence of the OpcA gene product is approx. 34.7 kilo Dalton.

SEQ ID NO 6 also shows the coding region of the zwf gene. The resulting amino acid sequence of the Zwf gene product is shown in SEQ ID NO 7. The molecular weight resulting from the amino acid sequence of the Zwf gene product is approx. 57.5 kilo Dalton.

Another procedure for at least partly determining the amino acid sequence of the OpcA protein and the Zwf protein comprises purifying the glucose 6-phosphate dehydrogenase enzyme protein to homogeneity by chromatographic methods. Methods and instructions for protein purification and preparation are described e.g. in the textbook by Schleifer and Wensink: Practical Methods in Molecular Biology (Springer Verlag, Berlin, Germany, 1981), in the handbook by Harris and Angal: Protein Purification Methods: A Practical Approach (IRL Press, Oxford, UK, 1989), in the textbook by Scopes: Protein Purification: Principles and Practice, $3^{rd}$ ed. (Springer Verlag, New York, USA, 1993) and in generally known textbooks and handbooks. The N-terminal amino acid sequence of the purified polypeptides can be determined by the method of N-terminal sequencing described by Edman (Archives of Biochemistry 22, 475 (1949)). Further methods and instructions for protein sequencing are described e.g. in Smith: Protein Sequencing Protocols: Methods in Molecular Biology, Vol. 64 and Vol. 112 (Humana Press, Totowa, N.J., USA, 1996) and in Kamp et al.: Protein Structure Analysis: Preparation, Characterization, and Microsequencing (Springer Verlag, New York, N.Y., USA, 1997).

It was possible to show in this manner that the enzyme glucose 6-phosphate dehydrogenase consists of two sub-units with in each case a molecular weight of approx. 30 kDa and approx. 60 kDa. The N-terminal amino acid sequence of the OpcA sub-unit and of the OpcA protein is shown in SEQ-ID-NO. 12. The N-terminal amino acid sequence of the Zwf sub-unit and of the Zwf protein is shown in SEQ-ID-NO. 11.

Coding DNA sequences which result from SEQ ID NO 1, SEQ ID NO 4, SEQ ID NO 6 or SEQ ID NO 9 by the degeneracy of the genetic code are also a constituent of the invention. In the same way, DNA sequences which hybridize with SEQ ID NO 4 or SEQ ID NO 9 or parts of SEQ ID NO 4 or SEQ ID NO 9 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID NO 3, SEQ ID NO 5, SEQ ID NO 8 or SEQ ID NO 10 are also a constituent of the invention.

Finally, DNA sequences which are prepared by the polymerase chain reaction (PCR) using primers which result from SEQ ID NO 4 or SEQ ID NO 9 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebi et al. (International Journal of Systematic Bacteriology (1991) 41: 255–260). Instructions for amplification of DNA sequences with the aid of the polymerase chain reaction (PCR) can be found by the expert, inter alia, in the handbook by Gait: Oligonukleotide synthesis: a practical approach (IRL Press, Oxford, UK, 1984) and in Newton and Graham: PCR (Spektrum Akademischer Verlag, Heidelberg, Germany, 1994).

The inventors have found that coryneform bacteria produce amino acids, in particular L-lysine, in an improved manner after over-expression of the opcA gene, optionally together with the zwf gene.

The use of endogenous genes in particular endogenous genes from coryneform bacteria is preferred. "Endogenous genes" or "endogenous nucleotide sequences" refer to genes, alleles or nucleotide sequences which are available in the population of a species.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification EPS 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, the opcA gene according to the invention was over-expressed with the aid of plasmids.

Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Figure 2:
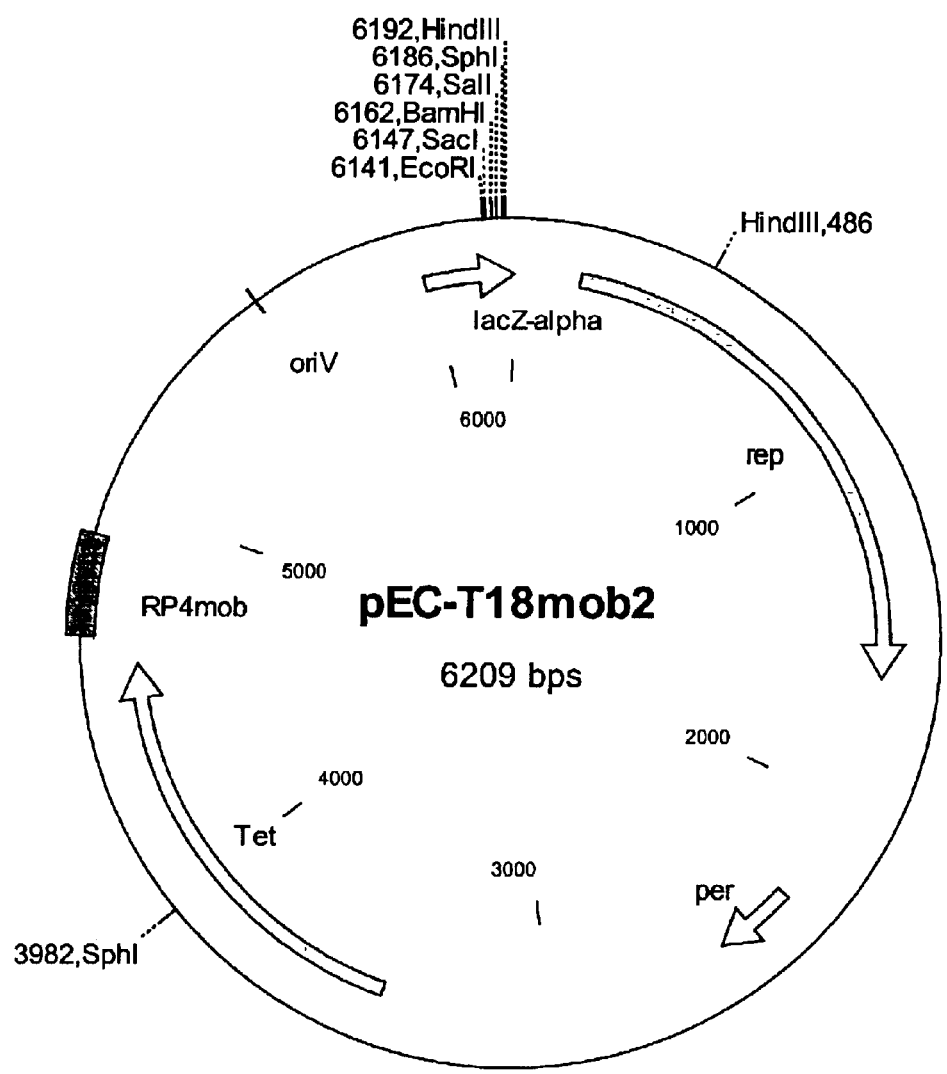
FIG. 2 is a map of the plasmid pEC-T18mob2.

The *E. coli—Corynebacterium glutamicum* shuttle vector pEC-T18mob2 shown in FIG. 2 was used as an example. After incorporation of the opcA gene and the zwf gene into the SphI/SalI cleavage site region of pEC-T18mob2, the plasmid pECzwfopcA shown in FIG. 3 was formed.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *Corynebacterium glutamicum*. Possible vectors are, for example, pSUP301 (Simon et al., Bio/Technology 1, 784–791 (1983)), pK18mob or pK19mob (Schafer et al., Gene 145, 69–73 (1994)), pGEM-T (Promega Corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:45104516) or pBGS8 (Spratt et al., 1986, Gene 41: 337–342). The plasmid vector which contains the gene to be amplified is then transferred into the desired strain of *Corynebacterium glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of amino acids, in particular L-lysine, to amplify or over-express one or more enzymes of the particular biosynthesis pathway, of glycolysis, of anaplerosis, of the pentose phosphate pathway or of amino acid export, in addition to the opcA gene, optionally together with the zwf gene.

Thus, for example, for the preparation of L-lysine, it may be advantageous for one or more genes chosen from the group consisting of the dapA gene which codes for dihydrodipicolinate synthase (EP-B 0 197 335), the lysC gene which codes for a feed back resistant aspartate kinase (Kalinowski et al. (1990), Molecular and General Genetics 224: 317–324), the gap gene which codes for glycerolaldehyde 3-phosphate dehydrogenase (Eikmanns (1992), Journal of Bacteriology 174:6076–6086), the pyc gene which codes for pyruvate carboxylase (DE-A-198 31 609), the tkt gene which codes for transketolase (accession number AB023377 of the databank of European Molecular Biology Laboratories (EMBL, Heidelberg, Germany)), the gnd gene which codes for 6-phosphogluconate dehydrogenase (JP-A-9-224662), the lysE gene which codes for the lysine export protein (DE-A-195 48 222), the zwa1 gene (DE 199 59 328.0; DSM 13115), or the eno gene which codes for enolase (DE: 199 41 478.5), the tal gene which codes for transaldolase (DSM 13263) to be amplified, in particular over-expressed, at the same time. The use of endogenous genes in particular endogenous genes from coryneform bacteria is preferred.

It may furthermore be advantageous for the production of amino acids, in particular L-lysine, at the same time to attenuate the pck gene which codes for phosphoenol pyruvate carboxykinase (DE 199 50 409.1 DSM 13047) and/or the pgi gene which codes for glucose 6-phosphate isomerase (U.S. Ser. No. 09/396,478, DSM 12969), or the poxB gene which codes for pyruvate oxidase (DE 199 51 975.7; DSM 13114), or the zwa2 gene (DE: 199 59 327.2; DSM 13113) in addition to the amplification of the opcA gene, optionally in combination with the zwf gene.

In this connection, the term "attenuation" means reducing or suppressing the intracellular activity or concentration of one or more enzymes or proteins in a microorganism, which enzymes or proteins are coded by the corresponding DNA, for example by using a weak promoter or a gene or allele which codes for a corresponding enzyme or protein which has a low activity or inactivates the corresponding enzyme or protein and optionally by combining these measures.

By attenuation measures, the activity or concentration of the corresponding enzyme or protein is in general reduced to 0 to 75%, 0 to 50%, 0 to 25%, 0 to 10% or 0 to 5% of the activity or concentration of the wild-type enzyme or protein or of the activity or concentration of the enzyme or protein in the starting microorganism.

In addition to over-expression of the opcA gene it may furthermore be advantageous for the production of amino acids, in particular L-lysine, to eliminate undesirable side reactions (Nakayama: "Breeding of Amino Acid Producing Microorganisms", in: Overproduction of Microbial Products, Krummphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of L-amino acids, in particular L-lysine. A summary of known culture methods are described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of L-amino acid has formed. This target is usually reached within 10 hours to 160 hours.

The analysis of L-amino acids can be carried out by anion exchange chromatography with subsequent ninhydrin derivation, as described by Spackman et al. (Analytical Chemistry, 30, (1958), 1190).

The following microorganism has been deposited at the Deutsche Sammlung für Mikroorganismen und Zellkulturen (DSMZ=German Collection of Microorganisms and Cell Cultures, Braunschweig, Germany) in accordance with the Budapest Treaty:

Corynebacterium glutamicum ATCC13032/pECzwfopcA as DSM 13264

SEQ ID NO 1 also contains the new devB gene. The process according to the invention is used for the fermentative preparation of amino acids, in particular L-lysine.

With reference to FIG. 1, the abbreviations that are used have the following meanings:
Neo r: Neomycin/kanamycin resistance
ColE1 ori: origin of replication of plasmid ColE1
CMV: Cytomegalovirus promoter
lacP: promotor of lac operon
lacZ: 5'-end of β-galactosidase gene (lacZa gene fragment)
SV40 3' splice 3' splice site of Simian Virus 40
SV40 polyA: polyadenylation site of Simian Virus 40
f1(−)ori: origin of replication of filamentousphage f1
SV40 ori: origin of replication of Simian Virus 40

Figure 3:
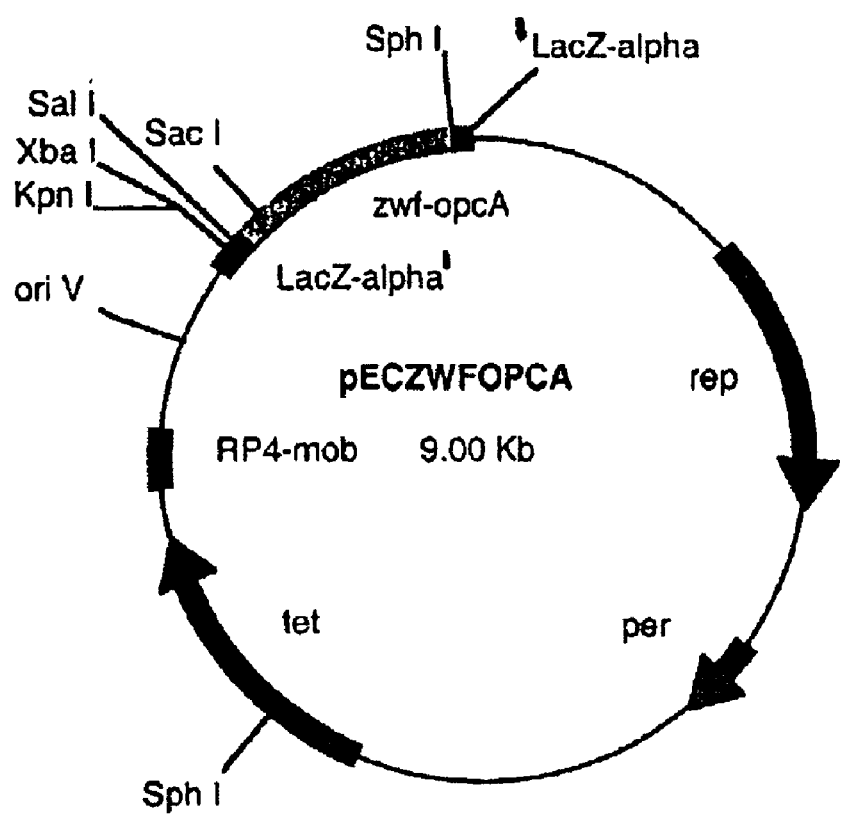
FIG. 3 is a map of the plasmid pECzwfopcA.

With reference to FIGS. 2 and 3, the abbreviations that are used have the following meanings:
Tet: Resistance gene for tetracycline
oriV: Plasmid-coded replication origin of *E. coli*
RP4mob: mob region for mobilizing the plasmid
rep: Plasmid-coded replication origin from *Corynebacterium glutamicum* plasmid pGA1
per: Gene for controlling the number of copies from PGA1
lacZ-alpha: lacZα a gene fragment (N-terminus) of the β-galactosidase gene
lacZalpha': 5'-Terminus of the lacZα gene fragment
'lacZalpha: 3'-Terminus of the lacZα gene fragment
zwf: zwf gene
opcA: opcA gene Certain other abbreviations are also used in the Figures, as follows:
ApaI: cleavage site of restriction enzyme ApaI
BamHI: cleavage site of restriction enzyme BamHI
ClaI: cleavage site of restriction enzyme ClaI
EcoRI: cleavage site of restriction enzyme EcoRI
HindIII: cleavage site of restriction enzyme HindIII
MstII: cleavage site of restriction enzyme MstII
NheI: cleavage site of restriction enzyme NheI
NsiI: cleavage site of restriction enzyme NsiI
SacI: cleavage site of restriction enzyme SacI
SalI: cleavage site of restriction enzyme SalI
SpeI: cleavage site of restriction enzyme SpeI
SphI: cleavage site of restriction enzyme SphI
SspI: cleavage site of restriction enzyme SspI
XbaI: cleavage site of restriction enzyme XbaI The following examples will further illustrate this invention. The molecular biology techniques, e.g. plasmid DNA isolation, restriction enzyme treatment, ligations, standard transformations of *Escherichia coli* etc. used are, (unless stated otherwise), described by Sambrook et al., (Molecular Cloning. A Laboratory Manual (1989) Cold Spring Harbor Laboratories, USA).

EXAMPLE 1

Construction of a Gene Library of *Corynebacterium glutamicum* Strain AS019

A DNA library of *Corynebacterium glutamicum* strain ASO19 (Yoshihama et al., Journal of Bacteriology 162, 591–597 (1985)) was constructed using λ Zap Express™ system, (Short et al., (1988) Nucleic Acids Research, 16: 7583–7600), as described by O'Donohue (O'Donohue, M. (1997). The Cloning and Molecular Analysis of Four Common Aromatic Amino Acid Biosynthetic Genes from *Corynebacterium glutamicum*. Ph.D. Thesis, National University of Ireland, Galway.). λ Zap Express™ kit was purchased from Stratagene (Stratagene, 11011 North Torrey Pines Rd., La Jolla, Calif. 92037.) and used according to the manufacturers instructions. AS019-DNA was digested with restriction enzyme Sau3A and ligated to BamHI treated and dephosphorylated λ Zap Express™ arms.

EXAMPLE 2

Cloning and Sequencing of the opcA and zwf Gene 2.1 Construction of a zwf Probe A radio-labeled oligonucleotide, internal to the zwf gene, was used to probe the ASO19 λ Zap Express™ library described above. The oligonucleotide was produced using degenerate PCR primers internal to the zwf gene. The degenerate nucleotide primers designed for the PCR amplification of zwf DNA fragments were as follows:
zwf1 (SEQ ID NO: 13): 5' ATY GAY CAC TAY YTS GGY AAR GA 3'
zwf2 (SEQ ID NO: 14): 5' RAA WGG MAC RCC YKS CCA 3'
with R=A+G; Y=C+T; W=A+T; M=A+C; S=G+C; K=T+G.
The estimated size of the resulting PCR product was 480 bp approximately.

Optimal PCR conditions were determined to be as follows:
35 cycles
94° C. for 1 minute
60° C. for 1 minute
72° C. for 30 seconds
2.5–3.5 mM $MgCl_2$
100–150 ng AS019 genomic DNA Sequence analysis of the resulting PCR product confirmed the product to be an internal portion of the zwf gene. Sequence analysis was carried out using the universal forward and reverse primers, and T7 sequencing kit from Pharmacia Biotech, (St. Albans, Herts, UK).

2.2 Cloning

Screening of the AS019 λ Zap Express™ library was carried out according to the λ Zap Express™ system protocol, (Stratagene, 11011 North Torrey Pines Rd., La Jolla, Calif. 92037.). Southern Blot analysis was then carried out on isolated clones. Southern transfer of DNA was as described in the Schleicher and Schuell protocols manual employing Nytran™ as membrane ("Nytran, Modified Nylon-66 Membrane Filters" (March 1987), Schleicher and Schuell, Dassel, Germany). Double stranded DNA fragments, generated using the same primers and optimal PCR conditions as described above, were radio-labeled with α-$^{32}$P-dCTP using the Multiprime™ DNA labelling kit from Amersham Life Science (Amersham Pharmacia Biotech UK Limited, Little Chalfont, Buckinghamshire, UK) according to the manufacturers instructions.

Pre-hybridization, hybridization and washing conditions were as described in the Schleicher and Schuell protocols manual. Autoradiography was carried out according to the procedure outlined in the handbook of Sambrook et al. using AgFa Curix RPIL film. Thus several zwf clones were identified. Plasmid DNA was isolated from one of the clones, designated pBOB102 (FIG. 1) and chosen for further analysis.

2.3 Sequencing

The Sanger Dideoxy chain termination method of Sanger et al. (Proceedings of the National Academy of Sciences USA 74, 5463–5467 (1977)) was used to sequence the cloned insert of pBOB102. The method was applied using the T7 sequencing kit and α-$^{35}$S-dCTP from Pharmacia Biotech (St. Albans, Hens, UK). Samples were electrophoresed for 3–8 hours on 6% polyacrylamide/urea gels in TBE buffer at a constant current of 50 mA, according to the Pharmacia cloning and sequencing instructions manual ("$^{T7}$ Sequencing™ Kit",ref.XY-010-00-19, Pharmacia Biotech, 1994). Initial sequence analysis was carried out using the universal forward and M13 reverse primers obtained from Pharmacia Biotech:

Universal forward primer (SEQ ID NO: 15):

5' GTA ATA CGA CTC ACT ATA GGG C 3'

M13 reverse primer (SEQ ID NO: 16):

5' GGA AAC AGC TAT GAC CAT G 3'

Internal primers were subsequently designed from the sequence obtained which allowed the entire opcA gene to be deduced. The sequences of the internal primers were as follows:

Internal primer 1 (SEQ ID NO: 17):

5' TCA ACC CTG AGT CCA CC 3'

Internal primer 2 (SEQ ID NO: 18):

5' CTG ACC ACG AGC GGA GG 3'

Internal primer 3 (SEQ ID NO: 19):

5' ATG GTG ATC TGG ACG TG 3'

Internal primer 4 (SEQ ID NO: 20):

5' CTG GCG ACT TGG CTC GA 3'

Internal primer 5 (SEQ ID NO: 21):

5' CTT CCG GAT ACC ACC ACC 3'

Sequence obtained was then analyzed using the DNA Strider program, (Marck (1988), Nucleic Acids Research 16: 1829–1836), version 1.0 on an Apple Macintosh computer. This program allowed for analyses such as restriction site usage, open reading frame analysis and codon usage determination. Searches between DNA sequence obtained and those in EMBL and Genbank databases were achieved using the BLAST program, (Altschul et al., (1997) Nucleic Acids Research, 25: 3389–3402). DNA and protein sequences were aligned using the Clustal V and Clustal W programs (Higgins and Sharp, 1988 Gene 73: 237–244).

The sequence thus obtained is shown in SEQ ID NO 6. The analysis of the nucleotide sequence obtained revealed an open reading frame of 957 base pairs which was designated as opcA gene. It codes for a protein of 319 amino acids shown in SEQ ID NO 8 and SEQ ID NO 10. The coding region of the zwf gene is also shown in SEQ ID NO 6. The amino acid sequence of the Zwf-Protein composed of 514 amino acids is shown in SEQ ID NO 7.

EXAMPLE 3

Preparation of a Genomic Cosmid Gene Library from Corynebacterium glutamicum ATCC 13032

Chromosomal DNA from Corynebacterium glutamicum ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extracts (Stratagene, La Jolla, USA, Product Description Gigapack II XL Packing Extract, Code no. 200217). For infection of the E. coli strain NM554 (Raleigh et al. 1988, Nucleic Acid Research 16:1563–1575) the cells were taken up in 10 mM MgSO$_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 µg/ml ampicillin. After incubation overnight at 37° C., recombinant individual clones were selected.

EXAMPLE 4

Isolation and Sequencing of the opcA and zwf Gene of ATCC 13032

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExH Gel Extraction Kit (Product No. 20021, Qiagen, Hilden, Germany). The DNA of the sequencing vector pZero-1, obtained from Invitrogen (Groningen, Holland, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol. Letters, 123:343–7) into the E. coli strain DH5αMCR (Grant, 1990, Proceedings of the National Academy of Sciences U.S.A., 87:4645–4649) and plated out on LB agar (Lennox, 1955, Virology, 1:190) with 50 µg/ml zeocin. The plasmid preparation of the recombinant clones was carried out with Biorobot 9600 (Product No. 900200, Qiagen, Hilden, Germany).

The sequencing was carried out by the dideoxy chain-stopping method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis were prepared with the XNIP program (Staden, 1986, Nucleic Acids Research, 14:217–231). Further analyses were carried out with the "BLAST search programs" (Altschul et al., 1997, Nucleic Acids Research, 25:3389–3402), against the non-redundant databank of the "National Center for Biotechnology Information" (NCBI, Bethesda, Md., USA).

The nucleotide sequence obtained is shown in SEQ ID NO 1. Analysis of the nucleotide sequence showed a coding region of 957 base pairs, which was called the opcA gene. The opcA gene, including its stop codon, is shown in SEQ ID NO 4. The opcA gene codes for a protein of 319 amino acids shown in SEQ ID NO 3 and SEQ ID NO 5.

EXAMPLE 5

Purification and N-terminal Sequencing of the Glucose-6-phosphate Dehydrogenase of *Corynebacterium glutamicum* ATCC 13032

5.1 Culture of Strain ATCC 13032

For purification of the glucose-6-phosphate dehydrogenase *Corynebacterium glutamicum* ATCC 13032 was grown aerobically on minimal medium at 30° C. in a Labfors fermentation system (Infors AG, Bottmingen, Switzerland). A preculture (Bacto® Brain Heart Infusion medium, Difco Laboratories, Detroit, USA) was incubated for 15 hours at 30° C. and used for inoculation of 2.5 l minimal medium. The medium contained the following constituents (amounts per liter): 20 g $(NH_4)_2SO_4$; 1 g $KH_2PO_4$; 1 g $K_2HPO_4$; 0.25 g $MgSO_4 \times 7\ H_2O$; 10 mg $CaCl_2$; 0.2 mg biotin; 30 mg protocatechuic acid; 1 mg $FeSO_4 \times 7\ H_2O$; 1 mg $MnSO_4 \times H_2O$; 0.1 mg $ZnSO_4 \times 7\ H_2O$; 0.02 mg $CuSO_4$; 0.002 mg $NiCl_2 \times 6\ H_2O$; 1.2 g HCl; 0.2 g polypropylene glycol; 75 mg tritriplex II and 100 g glucose. During fermentation sodium hydroxide was continuously added in order to keep the pH-value constant at 7.0. The cells were harvested in the late exponential growth phase. After centrifugation using an Avanti J-25 centrifuge and a JA10 rotor of Beckman (Fullerton, USA) at 6400 g for 15 minutes at 4° C. and washing in 100 mM TRIS-HCl pH 7.5 containing 10 mM $MgCl_2$ the sediment was stored at −20° C. until use.

5.2 Enzyme Purification

Disruption of cells was carried out in a disintegration system (Disintegrator S, BIOmatic, Rodgau-Hainhausen, Germany). The cells were previously resuspended in a pH 7.5 buffer consisting of 100 mM TRIS-HCl, 10 mM $MgCl_2$, 0.75 mM DTT and a mixture of several protease inhibitors (complete™, Roche, Mannheim, Germany). The ratio of the cell wet weight to the total suspension weight was adjusted to 0.3. After addition of 100 ml glass beads with a diameter of 0.1 to 0.25 mm (Fisher scientific, Dülsseldorf, Germany) per 100 ml total suspension volume, cell disruption was performed at 5000 rpm for 12 Minutes. A temperature increase during disruption was prevented by ice cooling. After removal of glass beads an ultracentifugation step was carried through using an L8-70 M centrifuge and a Ti45 rotor of Beckman (Fullerton, USA) at 235000 g for 90 minutes at 4° C. The supernatant was used as crude extract for the purification of the glucose-6-phosphate dehydrogenase. All purification steps were carried out with a Biosys2000 system of Beckman (Fullerton, USA).

The crude extract was applied to an XK 50/30 column (Pharmacia, Freiburg, Germany), which contained Fractogel EMD DEAE-650(S) material (Merck, Darmstadt). The total bed volume was 500 ml. The column was previously equilibrated with 50 mM TRIS-HCl pH 7.5 containing 30 mM $MgCl_2$ and 0.75 mM DTT. After application of the crude extract the column was washed with the same buffer containing 144 mM KCl. Elution was performed within 95 minutes by a linear KCl gradient from 144 mM up to 320 mM. The flow rate was 7.4 ml/min. The active fractions were pooled and concentrated in centriprep® 30 concentrators (Amicon, Beverly, USA) using a Varifuge 3.0R centrifuge (Heraeus, Hanau, Germany) at 1500 g and 4° C. By dilution with 50 mM TRIS-HCl pH 7.5 containing 30 mM $MgCl_2$ and 0.75 mM DTT the KCl concentration was adjusted to 40 mM. After that the partially purified glucose-6-phosphate dehydrogenase was applied to an XK26/20 column (Pharmacia, Freiburg, Germany), which was filled with 65 ml Red-Sepharose CL6B (Pharmacia, Freiburg, Germany). The column was equilibrated with 50 mM TRIS-HCl pH 7.5 containing 30 mM $MgCl_2$ and 0.75 mM DTT. Elution was carried out within 590 minutes by a linear 0–800 mM KCl gradient at a flow rate of 0.87 ml/min.

After pooling of the active glucose-6-phosphate dehydrogenase fractions, the KCl concentration was reduced to 10 mM in the same way as described above. After that the solution was applied to an XK16/20 column (Pharmacia, Freiburg, Germany), which contained 20 ml of a 2'5'-ADP-sepharose matrix (Pharmacia, Freiburg, Germany). The column was equilibrated with the same buffer as the Red-Sepharose CL6B column. Elution was performed by an 0 to 2 mM NADP linear gradient. The active glucose-6-phosphate dehydrogenase-fractions were pooled and applied to a gel filtration column.

For gel filtration a Superdex G200pg column (Pharmacia, Freiburg, Germany) with a diameter of 1.6 cm and a bed volume of 114 ml was used. The elution at a flow rate of 1 ml/min was carried through with 50 mM TRIS-HCl pH 7.5 containing 30 mM $MgCl_2$, 200 mM KCl and 0.75 mM DTT. The active fractions were pooled and concentrated by ultrafiltration in centriprep® 30 concentrators (Amicon, Beverly, USA). After addition of 50% (v/v) glycerol to the purified glucose-6-phosphate dehydrogenase solution it was stored at −20° C.

During the whole purification process the glucose-6-phosphate-dehydrogenase activity and the protein concentration were measured.

The assay system for determination of the glucose-6-phosphate-dehydrogenase-activity contained 50 mM TRIS-HCl pH 7.5, 10 mM $MgCl_2$, 1 mM NADP and 200 mM potassium glutamate. The reaction was initiated by addition of 4 mM glucose-6-phosphate and the formation of NADPH was followed by measuring the increase in absorbance at 340 nm at 30° C. Protein concentrations were determined spectrophotometrically after Coomassie Brilliant Blue staining (Stoscheck, Methods in Enzymology 182, 50–68 (1990)). As protein standard bovine serum albumin was used. All measurements were carried out using a UV-160 A photometer (Shimadzu, Kyoto, Japan).

The purity of the glucose-6-phosphate dehydrogenase was tested by danaturing discontinuous SDS-gelelectrophoresis according to the method of Laemmli (Laemmli, U.K., Nature 227, 680–685 (1970)). After the third purification step using 2'5'-ADO sapharose ligand affinity material two different proteins with molecular weights of ca. 60 kDa and 30 kDa could be obtained. These two proteins could not be separated by gel filtration chromatography. The specific activity of this preparation was determined as 213 U/mg protein.

N-terminal Sequencing

N-terminal sequencing of the purified glucose-6-P dehydrogenase was performed according to the procedure of Edman (Edman and Begg, European Journal of Biochemistry 1, 80–91 (1967)) using a Procise® Protein Sequencing System (Applied Biosystems, Foster City, USA).

For the 60 kDa protein the following N-terminal sequence was obtained: Xaa Xaa Xaa Xaa Xaa Pro Xaa Xaa Trp Xaa Asn Pro Leu Arg Asp. It is also shown in SEQ ID No 11.

For the 30 kDa protein the following N-terminal sequence was obtained: Met Ile Phe Xaa Leu Pro Asp Xaa Xaa Xaa Gln Gln Ile Ser Lys. It is also shown in SEQ ID No 12.

EXAMPLE 6 cloning of the zwf and opcA Genes into the pGEM T-vector

PCR was used to amplify DNA fragments containing the entire zwf and opcA genes of *Corynebacterium glutamicum* ATCC13032 and flanking upstream and downstream regions. PCR reactions were carried out using oligonucleotide primers designed from SEQ ID NO 1 and SEQ ID NO 6. Genomic DNA was isolated from *Corynebacterium glutamicum* ATCC13032 according to Heery and Dunican (Applied and Environmental Microbiology, 59: 791–799 (1993)) and used as template. The primers used were:

zwf fwd. primer (SEQ ID NO: 22):

5' AGA ATC AGC ACG CTG CAT CAG 3' opcA rev. primer (SEQ ID NO: 23):

5' AGT ATG GTG CGC GTA CTA 3'

PCR parameters were as follows:

35 cycles

95° C. for 3 minutes

94° C. for 1 minute

47° C. for 1 minute

72° C. for 45 seconds 2.5 mM MgCl2 approx. 150–200 ng DNA template.

The PCR product obtained was cloned into the commercially available PGEM-T vector purchased from Promega Corp. (pGEM-T Easy Vector System 1, cat. no. A1360, Promega UK, Southampton) using *E. coli* strain JM109 (Yanisch-Perron et al., Gene 33: 103–119 (1985)) as a host.

EXAMPLE 7

Preparation of the Shuttle Vector pEC-T18mob2

The *E. coli—C. glutamicum* shuttle vector pEC-T18mob2 was constructed according to the prior art.

The vector contains the replication region rep of the plasmid pGA1 including the replication effector per (U.S. Pat. No. 5,175,108; Nesvera et al., Journal of Bacteriology 179, 1525–1532 (1997)), the tetracycline resistance-imparting tetA(Z) gene of the plasmid pAG1 (U.S. Pat. No. 5,158,891; gene library entry at the National Center for Biotechnology Information (NCBI, Bethesda, Md., USA) with accession number AF121000), the replication region oriV of the plasmid pMB1 (Sutcliffe, Cold Spring Harbor Symposium on Quantitative Biology 43, 77–90 (1979)), the lacZα gene fragment including the lac promoter and a multiple cloning site (mcs) (Nonrander et al. Gene 26, 101–106 (1983)) and the mob region of the plasmid RP4 (Simon et al., (1983) Bio/Technology 1:784–791).

The vector constructed was transformed in the *E. coli* strain DH5 α (Hanahan, In: DNA cloning. A practical approach. Vol. I. IRL-Press, Oxford, Washington DC, USA). Selection for plasmid-carrying cells was made by plating out the transformation batch on LB agar (Sambrook et al., Molecular cloning: a laboratory manual. 2$^{nd}$ Ed. Cold Spring Harbor Laboratory Press, Cold Spring Harbor, N.Y.), which had been supplemented with 5 mg/l tetracycline. Plasmid DNA was isolated from a transformant with the aid of the QIAprep Spin Miniprep Kit from Qiagen and checked by restriction with the restriction enzyme EcoRI and HindIII subsequent agarose gel electrophoresis (0.8%).

The plasmid was called pEC-T18mob2 and is shown in FIG. 2. It is deposited in the form of the strain *Escherichia coli* K-12 strain DH5α/pEC-T18mob2 at the Deutsche Sammlung für Mikroorganismen und Zellkulturen (DSMZ= German Collection of Microorganisms and Cell Cultures, Braunschweig, Germany) as DSM 13244.

EXAMPLE 8

Expression of Glucose-6-phosphate Dehydrogenase in *Corynebacterium glutamicum*

The entire zwf and opcA genes were subsequently isolated from the pGEM T-vector containing these genes (see Example 6) on an SphI/SalI fragment and cloned into the lacZα SphI/SalI sites of the *E. coli-C. glutamicum* shuttle vector pEC-T18mob2 (see Example 7 and FIG. 2). This shuttle vector contains two SphI sites. The first is situated within the multiple cloning site of lacZα and the second is situated within the gene conferring tetracycline resistance. Tetracycline (Sigma-Aldrich, PO Box 2424, Wimborne, Dorset BH21 7YR, UK) (5 mg/l) was used therefore as a selective pressure as only those clones containing the intact tetracycline resistance gene would grow. This new construct was designated pECzwfopcA (FIG. 3). Restriction enzyme analysis with SacI (Bochringer Mannheim GmbH, Germany) revealed the correct orientation of the zwf and opcA genes in the lacZα gene of pEC-T18mob2 i.e. downstream the lac promotor. *Corynebacterium glutamicum* ATCC13032 (American Type Culture Collection, Manasas, Va., USA) was transformed with this construct and electrotransformants were selected on Luria agar supplemented with isopropyl-thiogalactopyranoside (IPTG), 5-bromo-4-chloro-3-indolyl-galactopyranoside (XGAL) and tetracycline at concentrations of 1 mM, 0.02% and 5 mg/l respectively. Agar plates were incubated for 48 hours at 30° C. Rapid plasmid preparations were carried out as described by O'Gara and Dunican, (Applied and Environmental Microbiology 61: 4477–4479 (1995)), and Sac I restriction confirmed the presence of required clones. One of the clones was designated ATCC13032/pECzwfopcA.

EXAMPLE 9

Preparation of Amino Acid Producers with an Amplified opcA Gene

The L-lysine-producing strain *Corynebacterium glutamicum* DSM5715 is described in EP-B-0435132 and the L-threonine-producing strain *Brevibacterium flavum* DSM5399 is described in EP-B-0385940. Both strains are deposited at the Deutsche Sammlung für Mikroorganismen und Zellkulturen [German Collection of Microorganisms and Cell Cultures] in Braunschweig (Germany) in accordance with the Budapest Treaty.

The strains DSM5715 and DSM5399 were transformed with the plasmid pECzwfopcA (Example 8) using the electroporation method described by Liebl et al., (FEMS Microbiology Letters, 53:299–303 (1989)) Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 5 mg/l tetracycline. Incubation was carried out for 2 days at 33° C.

The strains obtained in this way were called DSM5715/pECzwfopcA and DSM5399/pECzwfopcA.

EXAMPLE 10

Preparation of L-threonine

The *C. glutamicum* strain DSM5399/pECzwfopcA obtained in Example 9 was cultured in a nutrient medium suitable for the production of threonine and the threonine content in the culture supernatant was determined.

For this, the strain was first incubated on an agar plate with the corresponding antibiotic (brain-heart agar with tetracycline (5 mg/l)) for 24 hours at 33° C. Starting from this agar plate culture, a preculture was seeded (10 ml medium in a 100 ml conical flask). The complete medium CgIII was used as the medium for the preculture.

| | Medium Cg III |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4.

Tetracycline (5 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

| | Medium MM |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing was carried out in a 10 ml volume in a 100 ml conical flask with baffles. Tetracycline (5 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of threonine formed was determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | L-Threonine g/l |
|---|---|---|
| DSM5399 | 12.3 | 0.74 |
| DSM5399/pECzwfopcA | 9.9 | 1.0 |

EXAMPLE 11

Preparation of L-lysine

The *C. glutamicum* strain DSM5715/pECzwfopcA obtained in Example 9 was cultured in a nutrient medium suitable for the production of lysine and the lysine content in the culture supernatant was determined.

For this, the strain was first incubated on an agar plate with the corresponding antibiotic (brain-heart agar with tetracycline (5 mg/l)) for 24 hours at 33° C. Starting from this agar plate culture, a preculture was seeded (10 ml medium in a 100 ml conical flask). The complete medium CgIII was used as the medium for the preculture.

| | Medium Cg III |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4.

Tetracycline (5 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

| | Medium MM |
|---|---|
| CSL (corn steep liquor) | 5 g/l |
| MOPS (morpholinopropanesulfonic acid) | 20 g/l |
| Glucose (autoclaved separately) | 58 g/l |
| $(NH_4)_2SO_4$ | 25 g/l |
| $KH_2PO_4$ | 0.1 g/l |
| $MnSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing was carried out in a 10 ml volume in a 100 ml conical flask with baffles. Tetracycline (5 mg/l) was added.

Culturing was carried out at 33° C. and 80% atmospheric humidity.

After 72 hours, the OD was determined at a measurement wavelength of 660 nm with a Biomek 1000 (Beckmann Instruments GmbH, München). The amount of lysine formed was determined with an amino acid analyzer from Eppendorf-Biotronik (Hamburg, Germany) by ion exchange chromatography and post-column derivatization with ninhydrin detection.

The result of the experiment is shown in Table 2.

TABLE 2

| Strain | OD (660 nm) | L-Lysine HCl g/l |
|---|---|---|
| DSM5715 | 10.8 | 16.0 |
| DSM5715/pECzwfopcA | 8.1 | 17.1 |

What is claimed is:

1. An isolated polynucleotide consisting of a nucleotide sequence encoding a polypeptide consisting essentially of an amino acid sequence of SEQ ID NO: 3.

2. A vector comprising a promoter and the polynucleotide of claim 1.

3. A coryneform bacterium transformed with the vector of claim 2.

4. The coryneform bacterium of claim 3, wherein said bacterium is the species C. glutamicum.

5. An isolated polynucleotide consisting essentially of the nucleotide sequence of SEQ ID NO: 3.

6. A vector comprising a promoter and the polynucleotide of claim 5.

7. A host cell transformed with the vector of claim 6.

8. The host cell of claim 7, wherein said host is of the species C. glutamicum.

9. A polynucleotide that is completely complementary to the polynucleotide of claim 1.

10. A polynucleotide that is completely complementary to the polynucleotide of claim 5.

11. A vector comprising the isolated polynucleotide of claim 9 or 10.

12. A host cell transformed with the vector of claim 11.

13. The host cell of claim 11, wherein said host is of the species C. glutamicum.

14. An isolated nucleic acid comprising a nucleotide sequence selected from the group consisting of:

(a) a nucleotide sequence as set forth in SEQ ID NO: 4;

(b) a nucleotide sequence encoding the polypeptide as set forth in SEQ ID NO: 3; and (c) a nucleotide sequence fully complementary to (a) or (b).

15. A vector comprising the nucleic acid molecule of claim 14.

16. A host cell comprising the vector of claim 15.

17. The host cell of claim 16, wherein said host is of the species C. glutamicum.

* * * * *

SEQUENCE LISTING

<160> NUMBER OF SEQ ID NOS: 24

<210> SEQ ID NO 1
<211> LENGTH: 6995
<212> TYPE: DNA
<213> ORGANISM: Corynebacterium glutamicum
<220> FEATURE:
<223> OTHER INFORMATION: ATCC13032
<220> FEATURE:
<221> NAME/KEY: CDS
<222> LOCATION: (3658)..(5199)
<223> OTHER INFORMATION: zwf
<220> FEATURE:
<221> NAME/KEY: CDS
<222> LOCATION: (5217)..(6173)
<223> OTHER INFORMATION: opcA

<400> SEQUENCE: 1

```
cacatttgaa ccacagttgg ttataaaatg ggttcaacat cactatggtt agaggtgttg      60
acgggtcaga ttaagcaaag actactttcg gggtagatca cctttgccaa atttgaacca     120
attaacctaa gtcgtagatc tgatcatcgg atctaacgaa aacgaaccaa aacttttggtc    180
ccggtttaac ccaggaagga ttgaccacct tgacgctgtc acctgaactt caggcgctca     240
ctgtacgcaa ttacccctct gattggtccg atgtggacac caaggctgta gacactgttc     300
gtgtcctcgc tgcagacgct gtagaaaact gtggctccgg ccacccaggc accgcaatga     360
gcctggctcc ccttgcatac accttgtacc agcgggttat gaacgtagat ccacaggaca     420
ccaactgggc aggccgtgac cgcttcgttc tttcttgtgg ccactcctct ttgacccagt     480
acatccagct ttacttgggt ggattcggcc ttgagatgga tgacctgaag gctctgcgca     540
cctgggattc cttgaccccca ggacaccctg agtaccgcca caccaagggc gttgagatca    600
ccactggccc tcttggccag ggtcttgcat ctgcagttgg tatggccatg gctgctcgtc     660
gtgagcgtgg cctattcgac ccaaccgctg ctgagggcga tccccattc gaccaccaca     720
tctacgtcat tgcttctgat ggtgacctgc aggaaggtgt cacctctgag gcatcctcca    780
tcgctggcac ccagcagctg ggcaacctca tcgtgttctg ggatgacaac cgcatctcca    840
tcgaagacaa cactgagatc gctttcaacg aggacgttgt tgctcgttac aaggcttacg    900
gctggcagac cattgaggtt gaggctggcg aggacgttgc agcaatcgaa gctgcagtgg    960
ctgaggctaa gaaggacacc aagcgaccta ccttcatccg cgttcgcacc atcatcggct   1020
tcccagctcc aactatgatg aacaccggtg ctgtgcacgg tgctgctctt ggcgcagctg   1080
aggttgcagc aaccaagact gagcttggat tcgatcctga gctcacttc gcgatcgacg   1140
atgaggttat cgctcacacc cgctccctcg cagcgcgc tgcacagaag aaggctgcat   1200
ggcaggtcaa gttcgatgag tgggcagctg ccaaccctga gaacaaggct ctgttcgatc   1260
```

-continued

```
gcctgaactc ccgtgagctt ccagcgggct acgctgacga gctcccaaca tgggatgcag    1320
atgagaaggg cgtcgcaact cgtaaggctt ccgaggctgc acttcaggca ctgggcaaga    1380
cccttcctga gctgtggggc ggttccgctg acctcgcagg ttccaacaac accgtgatca    1440
agggctcccc ttccttcggc cctgagtcca tctccaccga gacctggtct gctgagcctt    1500
acggccgtaa cctgcacttc ggtatccgtg agcacgctat gggatccatc ctcaacggca    1560
tttccctcca cggtggcacc cgcccatacg gcggaacctt cctcatcttc tccgactaca    1620
tgcgtcctgc agttcgtctt gcagctctca tggagaccga cgcttactac gtctggaccc    1680
acgactccat cggtctgggc gaagatggcc caacccacca gcctgttgaa accttggctg    1740
cactgcgcgc catcccaggt ctgtccgtcc tgcgtcctgc agatgcgaac gagaccgccc    1800
aggcttgggc tgcagcactt gagtacaagg aaggccctaa gggtcttgca ctgacccgcc    1860
agaacgttcc tgttctggaa ggcaccaagg agaaggctgc tgaaggcgtt cgccgcggtg    1920
gctacgtcct ggttgagggt tccaaggaaa ccccagatgt gatcctcatg ggctccggct    1980
ccgaggttca gcttgcagtt aacgctgcga aggctctgga agctgagggc gttgcagctc    2040
gcgttgtttc cgttccttgc atggattggt tccaggagca ggacgcagag tacatcgagt    2100
ccgttctgcc tgcagctgtg accgctcgtg tgtctgttga agctggcatc gcaatgcctt    2160
ggtaccgctt cttgggcacc cagggccgtg ctgtctccct tgagcacttc ggtgcttctg    2220
cggattacca gaccctgttt gagaagttcg gcatcaccac cgatgcagtc gtggcagcgg    2280
ccaaggactc cattaacggt taattgccct gctgttttta gcttcaaccc ggggcaatat    2340
gattctccgg aattttattg ccccgggttg ttgttgttaa tcggtacaaa gggtcttaag    2400
cacatccctt acttgcctgc tctccttgag cacagttcaa gaacaattct tttaaggaaa    2460
atttagtttc atgtctcaca ttgatgatct tgcacagctc ggcacttcca cttggctcga    2520
cgacctctcc cgcgagcgca ttacttccgg caatctcagc caggttattg aggaaaagtc    2580
tgtagtcggt gtcaccacca acccagctat tttcgcagca gcaatgtcca agggcgattc    2640
ctacgacgct cagatcgcag agctcaaggc cgctggcgca tctgttgacc aggctgttta    2700
cgccatgagc atcgacgacg ttcgcaatgc ttgtgatctg ttcaccggca tcttcgagtc    2760
ctccaacggc tacgacggcc gcgtgtccat cgaggttgac ccacgtatct ctgctgaccg    2820
cgacgcaacc ctggctcagg ccaaggagct gtgggcaaag gttgatcgtc caaacgtcat    2880
gatcaagatc cctgcaaccc caggttcttt gccagcaatc accgacgctt ggctgagggg    2940
catcagcgtt aacgtcacct tgatcttctc cgttgctcgc taccgcgagg tcatcgctgc    3000
gttcatcgag ggcatcaagc aggctgctgc aaacggccac gacgtctcca agatccactc    3060
tgtggcttcc ttcttcgtct cccgcgtcga cgttgagatc gacaagcgcc tcgaggcaat    3120
cggatccgat gaggctttgg ctctgcgcgg caaggcaggc gttgccaacg ctcagcgcgc    3180
ttacgctgtg tacaaggagc ttttcgacgc cgccgagctg cctgaaggtg ccaacactca    3240
gcgcccactg tgggcatcca ccggcgtgaa gaacccgcg tacgctgcaa ctctttacgt    3300
ttccgagctg gctggtccaa acaccgtcaa caccatgcca gaaggcacca tcgacgcggt    3360
tctggagcag ggcaacctgc acggtgacac cctgtccaac tccgcggcag aagctgacgc    3420
tgtgttctcc cagcttgagg ctctgggcgt tgacttggca gatgtcttcc aggtcctgga    3480
gaccgagggt gtggacaagt tcgttgcttc ttggagcgaa ctgcttgagt ccatggaagc    3540
tcgcctgaag tagaatcagc acgctgcatc agtaacggcg acatgaaatc gaattagttc    3600
```

```
gatcttatgt ggccgttaca catctttcat taaagaaagg atcgtgacac taccatc      3657 gtg agc aca aac acg acc ccc tcc agc tgg aca aac cca ctg cgc gac      3705
Met Ser Thr Asn Thr Thr Pro Ser Ser Trp Thr Asn Pro Leu Arg Asp
 1               5                  10                  15 ccg cag gat aaa cga ctc ccc cgc atc gct ggc cct tcc ggc atg gtg      3753
Pro Gln Asp Lys Arg Leu Pro Arg Ile Ala Gly Pro Ser Gly Met Val
             20                  25                  30 atc ttc ggt gtc act ggc gac ttg gct cga aag aag ctg ctc ccc gcc      3801
Ile Phe Gly Val Thr Gly Asp Leu Ala Arg Lys Lys Leu Leu Pro Ala
         35                  40                  45 att tat gat cta gca aac cgc gga ttg ctg ccc cca gga ttc tcg ttg      3849
Ile Tyr Asp Leu Ala Asn Arg Gly Leu Leu Pro Pro Gly Phe Ser Leu
     50                  55                  60 gta ggt tac ggc cgc cgc gaa tgg tcc aaa gaa gac ttt gaa aaa tac      3897
Val Gly Tyr Gly Arg Arg Glu Trp Ser Lys Glu Asp Phe Glu Lys Tyr
 65                  70                  75                  80 gta cgc gat gcc gca agt gct ggt gct cgt acg gaa ttc cgt gaa aat      3945
Val Arg Asp Ala Ala Ser Ala Gly Ala Arg Thr Glu Phe Arg Glu Asn
                 85                  90                  95 gtt tgg gag cgc ctc gcc gag ggt atg gaa ttt gtt cgc ggc aac ttt      3993
Val Trp Glu Arg Leu Ala Glu Gly Met Glu Phe Val Arg Gly Asn Phe
            100                 105                 110 gat gat gat gca gct ttc gac aac ctc gct gca aca ctc aag cgc atc      4041
Asp Asp Asp Ala Ala Phe Asp Asn Leu Ala Ala Thr Leu Lys Arg Ile
        115                 120                 125 gac aaa acc cgc ggc acc gcc ggc aac tgg gct tac tac ctg tcc att      4089
Asp Lys Thr Arg Gly Thr Ala Gly Asn Trp Ala Tyr Tyr Leu Ser Ile
    130                 135                 140 cca cca gat tcc ttc aca gcg gtc tgc cac cag ctg gag cgt tcc ggc      4137
Pro Pro Asp Ser Phe Thr Ala Val Cys His Gln Leu Glu Arg Ser Gly
145                 150                 155                 160 atg gct gaa tcc acc gaa gaa gca tgg cgc cgc gtg atc atc gag aag      4185
Met Ala Glu Ser Thr Glu Glu Ala Trp Arg Arg Val Ile Ile Glu Lys
                165                 170                 175 cct ttc ggc cac aac ctc gaa tcc gca cac gag ctc aac cag ctg gtc      4233
Pro Phe Gly His Asn Leu Glu Ser Ala His Glu Leu Asn Gln Leu Val
            180                 185                 190 aac gca gtc ttc cca gaa tct tct gtg ttc cgc atc gac cac tat ttg      4281
Asn Ala Val Phe Pro Glu Ser Ser Val Phe Arg Ile Asp His Tyr Leu
        195                 200                 205 ggc aag gaa aca gtt caa aac atc ctg gct ctg cgt ttt gct aac cag      4329
Gly Lys Glu Thr Val Gln Asn Ile Leu Ala Leu Arg Phe Ala Asn Gln
    210                 215                 220 ctg ttt gag cca ctg tgg aac tcc aac tac gtt gac cac gtc cag atc      4377
Leu Phe Glu Pro Leu Trp Asn Ser Asn Tyr Val Asp His Val Gln Ile
225                 230                 235                 240 acc atg gct gaa gat att ggc ttg ggt gga cgt gct ggt tac tac gac      4425
Thr Met Ala Glu Asp Ile Gly Leu Gly Gly Arg Ala Gly Tyr Tyr Asp
                245                 250                 255 ggc atc ggc gca gcc cgc gac gtc atc cag aac cac ctg atc cag ctc      4473
Gly Ile Gly Ala Ala Arg Asp Val Ile Gln Asn His Leu Ile Gln Leu
            260                 265                 270 ttg gct ctg gtt gcc atg gaa gaa cca att tct ttc gtg cca gcg cag      4521
Leu Ala Leu Val Ala Met Glu Glu Pro Ile Ser Phe Val Pro Ala Gln
        275                 280                 285 ctg cag gca gaa aag atc aag gtg ctc tct gcg aca aag ccg tgc tac      4569
Leu Gln Ala Glu Lys Ile Lys Val Leu Ser Ala Thr Lys Pro Cys Tyr
    290                 295                 300
```

-continued

| | |
|---|---|
| cca ttg gat aaa acc tcc gct cgt ggt cag tac gct gcc ggt tgg cag<br>Pro Leu Asp Lys Thr Ser Ala Arg Gly Gln Tyr Ala Ala Gly Trp Gln<br>305                                 310                           315                           320 | 4617 |
| ggc tct gag tta gtc aag gga ctt cgc gaa gaa gat ggc ttc aac cct<br>Gly Ser Glu Leu Val Lys Gly Leu Arg Glu Glu Asp Gly Phe Asn Pro<br>                        325                           330                           335 | 4665 |
| gag tcc acc act gag act ttt gcg gct tgt acc tta gag atc acg tct<br>Glu Ser Thr Thr Glu Thr Phe Ala Ala Cys Thr Leu Glu Ile Thr Ser<br>                   340                          345                          350 | 4713 |
| cgt cgc tgg gct ggt gtg ccg ttc tac ctg cgc acc ggt aag cgt ctt<br>Arg Arg Trp Ala Gly Val Pro Phe Tyr Leu Arg Thr Gly Lys Arg Leu<br>           355                          360                          365 | 4761 |
| ggt cgc cgt gtt act gag att gcc gtg gtg ttt aaa gac gca cca cac<br>Gly Arg Arg Val Thr Glu Ile Ala Val Val Phe Lys Asp Ala Pro His<br>370                                 375                           380 | 4809 |
| cag cct ttc gac ggc gac atg act gta tcc ctt ggc caa aac gcc atc<br>Gln Pro Phe Asp Gly Asp Met Thr Val Ser Leu Gly Gln Asn Ala Ile<br>385                                 390                         395                       400 | 4857 |
| gtg att cgc gtg cag cct gat gaa ggt gtg ctc atc cgc ttc ggt tcc<br>Val Ile Arg Val Gln Pro Asp Glu Gly Val Leu Ile Arg Phe Gly Ser<br>                   405                          410                          415 | 4905 |
| aag gtt cca ggt tct gcc atg gaa gtc cgt gac gtc aac atg gac ttc<br>Lys Val Pro Gly Ser Ala Met Glu Val Arg Asp Val Asn Met Asp Phe<br>           420                          425                          430 | 4953 |
| tcc tac tca gaa tcc ttc act gaa gaa tca cct gaa gca tac gag cgc<br>Ser Tyr Ser Glu Ser Phe Thr Glu Glu Ser Pro Glu Ala Tyr Glu Arg<br>435                               440                         445 | 5001 |
| ctc att ttg gat gcg ctg tta gat gaa tcc agc ctc ttc cct acc aac<br>Leu Ile Leu Asp Ala Leu Leu Asp Glu Ser Ser Leu Phe Pro Thr Asn<br>         450                          455                          460 | 5049 |
| gag gaa gtg gaa ctg agc tgg aag att ctg gat cca att ctt gaa gca<br>Glu Glu Val Glu Leu Ser Trp Lys Ile Leu Asp Pro Ile Leu Glu Ala<br>465                               470                         475                       480 | 5097 |
| tgg gat gcc gat gga gaa cca gag gat tac cca gcg ggt acg tgg ggt<br>Trp Asp Ala Asp Gly Glu Pro Glu Asp Tyr Pro Ala Gly Thr Trp Gly<br>                   485                          490                          495 | 5145 |
| cca aag agc gct gat gaa atg ctt tcc cgc aac ggt cac acc tgg cgc<br>Pro Lys Ser Ala Asp Glu Met Leu Ser Arg Asn Gly His Thr Trp Arg<br>           500                          505                          510 | 5193 |
| agg cca taa tttaggggca aaaa atg atc ttt gaa ctt ccg gat acc acc<br>Arg Pro                           Met Ile Phe Glu Leu Pro Asp Thr Thr<br>                                           515                           520 | 5243 |
| acc cag caa att tcc aag acc cta act cga ctg cgt gaa tcg ggc acc<br>Thr Gln Gln Ile Ser Lys Thr Leu Thr Arg Leu Arg Glu Ser Gly Thr<br>525                               530                           535 | 5291 |
| cag gtc acc acc ggc cga gtg ctc acc ctc atc gtg gtc act gac tcc<br>Gln Val Thr Thr Gly Arg Val Leu Thr Leu Ile Val Val Thr Asp Ser<br>540                             545                           550                       555 | 5339 |
| gaa agc gat gtc gct gca gtt acc gag tcc acc aat gaa gcc tcg cgc<br>Glu Ser Asp Val Ala Ala Val Thr Glu Ser Thr Asn Glu Ala Ser Arg<br>                   560                          565                          570 | 5387 |
| gag cac cca tct cgc gtg atc att ttg gtg gtt ggc gat aaa act gca<br>Glu His Pro Ser Arg Val Ile Ile Leu Val Val Gly Asp Lys Thr Ala<br>                         575                           580                       585 | 5435 |
| gaa aac aaa gtt gac gca gaa gtc cgt atc ggt ggc gac gct ggt gct<br>Glu Asn Lys Val Asp Ala Glu Val Arg Ile Gly Gly Asp Ala Gly Ala<br>                       590                          595                       600 | 5483 |
| tcc gag atg atc atc atg cat ctc aac gga cct gtc gct gac aag ctc<br>Ser Glu Met Ile Ile Met His Leu Asn Gly Pro Val Ala Asp Lys Leu<br>605                             610                           615 | 5531 |

```
cag tat gtc gtc aca cca ctg ttg ctt cct gac acc ccc atc gtt gct      5579
Gln Tyr Val Val Thr Pro Leu Leu Leu Pro Asp Thr Pro Ile Val Ala
620                 625                 630                 635 tgg tgg cca ggt gaa tca cca aag aat cct tcc cag gac cca att gga      5627
Trp Trp Pro Gly Glu Ser Pro Lys Asn Pro Ser Gln Asp Pro Ile Gly
                640                 645                 650 cgc atc gca caa cga cgc atc act gat gct ttg tac gac cgt gat gac      5675
Arg Ile Ala Gln Arg Arg Ile Thr Asp Ala Leu Tyr Asp Arg Asp Asp
            655                 660                 665 gca cta gaa gat cgt gtt gag aac tat cac cca ggt gat acc gac atg      5723
Ala Leu Glu Asp Arg Val Glu Asn Tyr His Pro Gly Asp Thr Asp Met
        670                 675                 680 acg tgg gcg cgc ctt acc cag tgg cgg gga ctt gtt gcc tcc tca ttg      5771
Thr Trp Ala Arg Leu Thr Gln Trp Arg Gly Leu Val Ala Ser Ser Leu
    685                 690                 695 gat cac cca cca cac agc gaa atc act tcc gtg agg ctg acc ggt gca      5819
Asp His Pro Pro His Ser Glu Ile Thr Ser Val Arg Leu Thr Gly Ala
700                 705                 710                 715 agc ggc agt acc tcg gtg gat ttg gct gca ggc tgg ttg gcg cgg agg      5867
Ser Gly Ser Thr Ser Val Asp Leu Ala Ala Gly Trp Leu Ala Arg Arg
                720                 725                 730 ctg aaa gtg cct gtg atc cgc gag gtg aca gat gct ccc acc gtg cca      5915
Leu Lys Val Pro Val Ile Arg Glu Val Thr Asp Ala Pro Thr Val Pro
            735                 740                 745 acc gat gag ttt ggt act cca ctg ctg gct atc cag cgc ctg gag atc      5963
Thr Asp Glu Phe Gly Thr Pro Leu Leu Ala Ile Gln Arg Leu Glu Ile
        750                 755                 760 gtt cgc acc acc ggc tcg atc atc atc acc atc tat gac gct cat acc      6011
Val Arg Thr Thr Gly Ser Ile Ile Ile Thr Ile Tyr Asp Ala His Thr
    765                 770                 775 ctt cag gta gag atg ccg gaa tcc ggc aat gcc cca tcg ctg gtg gct      6059
Leu Gln Val Glu Met Pro Glu Ser Gly Asn Ala Pro Ser Leu Val Ala
780                 785                 790                 795 att ggt cgt cga agt gag tcc gac tgc ttg tct gag gag ctt cgc cac      6107
Ile Gly Arg Arg Ser Glu Ser Asp Cys Leu Ser Glu Glu Leu Arg His
                800                 805                 810 atg gat cca gat ttg ggc tac cag cac gca cta tcc ggc ttg tcc agc      6155
Met Asp Pro Asp Leu Gly Tyr Gln His Ala Leu Ser Gly Leu Ser Ser
            815                 820                 825 gtc aag ctg gaa acc gtc taaggagaaa tacaacacta tggttgatgt             6203
Val Lys Leu Glu Thr Val
            830 agtacgcgca cgcgatactg aagatttggt tgcacaggct gcctccaaat tcattgaggt    6263 tgttgaagca gcaactgcca ataatggcac cgcacaggta gtgctcaccg gtggtggcgc    6323 cggcatcaag ttgctggaaa agctcagcgt tgatgcggct gaccttgcct gggatcgcat    6383 tcatgtgttc ttcggcgatg agcgcaatgt ccctgtcagt gattctgagt ccaatgaggg    6443 ccaggctcgt gaggcactgt tgtccaaggt ttctatccct gaagccaaca ttcacggata    6503 tggtctcggc gacgtagatc ttgcagaggc agcccgcgct tacgaagctg tgttggatga    6563 attcgcacca aacggctttg atcttcacct gctcggcatg ggtggcgaag ccatatcaa     6623 ctccctgttc cctcacaccg atgcagtcaa ggaatcctcc gcaaaggtca tcgcggtgtt    6683 tgattcccct aagcctcctt cagagcgtgc aactctaacc cttcctgcgg ttcactccgc    6743 aaagcgcgtg tggttgctgg tttctggtgc ggagaaggct gaggcagctg cggcgatcgt    6803 caacggtgag cctgctgttg agtggcctgc tgctggagct accggatctg aggaaacggt    6863
```

```
attgttcttg gctgatgatg ctgcaggaaa tctctaagca gcgccagctc taacaagaag    6923
ctttaacaag aagctctaac gaaaagcact aacaaactaa tccgggtgcg aaccttcatc    6983
tgaatcgatg ga                                                        6995
```

<210> SEQ ID NO 2
<211> LENGTH: 514
<212> TYPE: PRT
<213> ORGANISM: Corynebacterium glutamicum
<220> FEATURE:
<223> OTHER INFORMATION: ATCC13032

<400> SEQUENCE: 2

```
Met Ser Thr Asn Thr Thr Pro Ser Ser Trp Thr Asn Pro Leu Arg Asp
  1               5                  10                  15

Pro Gln Asp Lys Arg Leu Pro Arg Ile Ala Gly Pro Ser Gly Met Val
             20                  25                  30

Ile Phe Gly Val Thr Gly Asp Leu Ala Arg Lys Lys Leu Leu Pro Ala
         35                  40                  45

Ile Tyr Asp Leu Ala Asn Arg Gly Leu Leu Pro Pro Gly Phe Ser Leu
     50                  55                  60

Val Gly Tyr Gly Arg Arg Glu Trp Ser Lys Glu Asp Phe Glu Lys Tyr
 65                  70                  75                  80

Val Arg Asp Ala Ala Ser Ala Gly Ala Arg Thr Glu Phe Arg Glu Asn
                 85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335
```

-continued

```
Glu Ser Thr Thr Glu Thr Phe Ala Ala Cys Thr Leu Glu Ile Thr Ser
            340                 345                 350
Arg Arg Trp Ala Gly Val Pro Phe Tyr Leu Arg Thr Gly Lys Arg Leu
        355                 360                 365
Gly Arg Arg Val Thr Glu Ile Ala Val Val Phe Lys Asp Ala Pro His
    370                 375                 380
Gln Pro Phe Asp Gly Asp Met Thr Val Ser Leu Gly Gln Asn Ala Ile
385                 390                 395                 400
Val Ile Arg Val Gln Pro Asp Glu Gly Val Leu Ile Arg Phe Gly Ser
                405                 410                 415
Lys Val Pro Gly Ser Ala Met Glu Val Arg Asp Val Asn Met Asp Phe
            420                 425                 430
Ser Tyr Ser Glu Ser Phe Thr Glu Glu Ser Pro Glu Ala Tyr Glu Arg
        435                 440                 445
Leu Ile Leu Asp Ala Leu Leu Asp Glu Ser Ser Leu Phe Pro Thr Asn
    450                 455                 460
Glu Glu Val Glu Leu Ser Trp Lys Ile Leu Asp Pro Ile Leu Glu Ala
465                 470                 475                 480
Trp Asp Ala Asp Gly Glu Pro Glu Asp Tyr Pro Ala Gly Thr Trp Gly
                485                 490                 495
Pro Lys Ser Ala Asp Glu Met Leu Ser Arg Asn Gly His Thr Trp Arg
            500                 505                 510
Arg Pro

<210> SEQ ID NO 3
<211> LENGTH: 319
<212> TYPE: PRT
<213> ORGANISM: Corynebacterium glutamicum
<220> FEATURE:
<223> OTHER INFORMATION: ATCC13032

<400> SEQUENCE: 3

Met Ile Phe Glu Leu Pro Asp Thr Thr Gln Gln Ile Ser Lys Thr
  1               5                  10                  15
Leu Thr Arg Leu Arg Glu Ser Gly Thr Gln Val Thr Thr Gly Arg Val
             20                  25                  30
Leu Thr Leu Ile Val Val Thr Asp Ser Glu Ser Asp Val Ala Ala Val
         35                  40                  45
Thr Glu Ser Thr Asn Glu Ala Ser Arg Glu His Pro Ser Arg Val Ile
     50                  55                  60
Ile Leu Val Val Gly Asp Lys Thr Ala Glu Asn Lys Val Asp Ala Glu
 65                  70                  75                  80
Val Arg Ile Gly Gly Asp Ala Gly Ala Ser Glu Met Ile Ile Met His
                 85                  90                  95
Leu Asn Gly Pro Val Ala Asp Lys Leu Gln Tyr Val Val Thr Pro Leu
            100                 105                 110
Leu Leu Pro Asp Thr Pro Ile Val Ala Trp Trp Pro Gly Glu Ser Pro
        115                 120                 125
Lys Asn Pro Ser Gln Asp Pro Ile Gly Arg Ile Ala Gln Arg Ile
    130                 135                 140
Thr Asp Ala Leu Tyr Asp Arg Asp Ala Leu Glu Asp Arg Val Glu
145                 150                 155                 160
Asn Tyr His Pro Gly Asp Thr Asp Met Thr Trp Ala Arg Leu Thr Gln
                165                 170                 175
Trp Arg Gly Leu Val Ala Ser Ser Leu Asp His Pro Pro His Ser Glu
```

-continued

```
                    180                 185                 190
Ile Thr Ser Val Arg Leu Thr Gly Ala Ser Gly Ser Thr Ser Val Asp
            195                 200                 205

Leu Ala Ala Gly Trp Leu Ala Arg Arg Leu Lys Val Pro Val Ile Arg
210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
                275                 280                 285

Asp Cys Leu Ser Glu Glu Leu Arg His Met Asp Pro Asp Leu Gly Tyr
        290                 295                 300

Gln His Ala Leu Ser Gly Leu Ser Ser Val Lys Leu Glu Thr Val
305                 310                 315

<210> SEQ ID NO 4
<211> LENGTH: 960
<212> TYPE: DNA
<213> ORGANISM: Corynebacterium glutamicum
<220> FEATURE:
<223> OTHER INFORMATION: ATCC13032
<220> FEATURE:
<221> NAME/KEY: CDS
<222> LOCATION: (1)..(957)
<223> OTHER INFORMATION: opcA

<400> SEQUENCE: 4 atg atc ttt gaa ctt ccg gat acc acc acc cag caa att tcc aag acc     48
Met Ile Phe Glu Leu Pro Asp Thr Thr Thr Gln Gln Ile Ser Lys Thr
1               5                   10                  15 cta act cga ctg cgt gaa tcg ggc acc cag gtc acc acc ggc cga gtg     96
Leu Thr Arg Leu Arg Glu Ser Gly Thr Gln Val Thr Thr Gly Arg Val
            20                  25                  30 ctc acc ctc atc gtg gtc act gac tcc gaa agc gat gtc gct gca gtt    144
Leu Thr Leu Ile Val Val Thr Asp Ser Glu Ser Asp Val Ala Ala Val
        35                  40                  45 acc gag tcc acc aat gaa gcc tcg cgc gag cac cca tct cgc gtg atc    192
Thr Glu Ser Thr Asn Glu Ala Ser Arg Glu His Pro Ser Arg Val Ile
    50                  55                  60 att ttg gtg gtt ggc gat aaa act gca gaa aac aaa gtt gac gca gaa    240
Ile Leu Val Val Gly Asp Lys Thr Ala Glu Asn Lys Val Asp Ala Glu
65                  70                  75                  80 gtc cgt atc ggt ggc gac gct ggt gct tcc gag atg atc atc atg cat    288
Val Arg Ile Gly Gly Asp Ala Gly Ala Ser Glu Met Ile Ile Met His
                85                  90                  95 ctc aac gga cct gtc gct gac aag ctc cag tat gtc gtc aca cca ctg    336
Leu Asn Gly Pro Val Ala Asp Lys Leu Gln Tyr Val Val Thr Pro Leu
            100                 105                 110 ttg ctt cct gac acc ccc atc gtt gct tgg tgg cca ggt gaa tca cca    384
Leu Leu Pro Asp Thr Pro Ile Val Ala Trp Trp Pro Gly Glu Ser Pro
        115                 120                 125 aag aat cct tcc cag gac cca att gga cgc atc gca caa cga cgc atc    432
Lys Asn Pro Ser Gln Asp Pro Ile Gly Arg Ile Ala Gln Arg Arg Ile
    130                 135                 140 act gat gct ttg tac gac cgt gat gac gca cta gaa gat cgt gtt gag    480
Thr Asp Ala Leu Tyr Asp Arg Asp Asp Ala Leu Glu Asp Arg Val Glu
145                 150                 155                 160
```

-continued

```
aac tat cac cca ggt gat acc gac atg acg tgg gcg cgc ctt acc cag    528
Asn Tyr His Pro Gly Asp Thr Asp Met Thr Trp Ala Arg Leu Thr Gln
                165                 170                 175 tgg cgg gga ctt gtt gcc tcc tca ttg gat cac cca cac agc gaa        576
Trp Arg Gly Leu Val Ala Ser Ser Leu Asp His Pro His Ser Glu
        180                 185                 190 atc act tcc gtg agg ctg acc ggt gca agc ggc agt acc tcg gtg gat    624
Ile Thr Ser Val Arg Leu Thr Gly Ala Ser Gly Ser Thr Ser Val Asp
    195                 200                 205 ttg gct gca ggc tgg ttg gcg cgg agg ctg aaa gtg cct gtg atc cgc    672
Leu Ala Ala Gly Trp Leu Ala Arg Arg Leu Lys Val Pro Val Ile Arg
210                 215                 220 gag gtg aca gat gct ccc acc gtg cca acc gat gag ttt ggt act cca    720
Glu Val Thr Asp Ala Pro Thr Val Pro Thr Asp Glu Phe Gly Thr Pro
225                 230                 235                 240 ctg ctg gct atc cag cgc ctg gag atc gtt cgc acc acc ggc tcg atc    768
Leu Leu Ala Ile Gln Arg Leu Glu Ile Val Arg Thr Thr Gly Ser Ile
                245                 250                 255 atc atc acc atc tat gac gct cat acc ctt cag gta gag atg ccg gaa    816
Ile Ile Thr Ile Tyr Asp Ala His Thr Leu Gln Val Glu Met Pro Glu
            260                 265                 270 tcc ggc aat gcc cca tcg ctg gtg gct att ggt cgt cga agt gag tcc    864
Ser Gly Asn Ala Pro Ser Leu Val Ala Ile Gly Arg Arg Ser Glu Ser
        275                 280                 285 gac tgc ttg tct gag gag ctt cgc cac atg gat cca gat ttg ggc tac    912
Asp Cys Leu Ser Glu Glu Leu Arg His Met Asp Pro Asp Leu Gly Tyr
    290                 295                 300 cag cac gca cta tcc ggc ttg tcc agc gtc aag ctg gaa acc gtc taa    960
Gln His Ala Leu Ser Gly Leu Ser Ser Val Lys Leu Glu Thr Val
305                 310                 315
```

<210> SEQ ID NO 5
<211> LENGTH: 319
<212> TYPE: PRT
<213> ORGANISM: Corynebacterium glutamicum
<220> FEATURE:
<223> OTHER INFORMATION: ATCC13032

<400> SEQUENCE: 5

```
Met Ile Phe Glu Leu Pro Asp Thr Thr Gln Gln Ile Ser Lys Thr
1               5                   10                  15

Leu Thr Arg Leu Arg Glu Ser Gly Thr Gln Val Thr Thr Gly Arg Val
                20                  25                  30

Leu Thr Leu Ile Val Val Thr Asp Ser Glu Ser Asp Val Ala Ala Val
            35                  40                  45

Thr Glu Ser Thr Asn Glu Ala Ser Arg Glu His Pro Ser Arg Val Ile
        50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Asp Ala Leu Glu Asp Arg Val Glu
```

-continued

```
                145                 150                 155                 160
Asn Tyr His Pro Gly Asp Thr Asp Met Thr Trp Ala Arg Leu Thr Gln
                    165                 170                 175
Trp Arg Gly Leu Val Ala Ser Ser Leu Asp His Pro His Ser Glu
                180                 185                 190
Ile Thr Ser Val Arg Leu Thr Gly Ala Ser Gly Ser Thr Ser Val Asp
            195                 200                 205
Leu Ala Ala Gly Trp Leu Ala Arg Arg Leu Lys Val Pro Val Ile Arg
        210                 215                 220
Glu Val Thr Asp Ala Pro Thr Val Pro Thr Asp Glu Phe Gly Thr Pro
225                 230                 235                 240
Leu Leu Ala Ile Gln Arg Leu Glu Ile Val Arg Thr Thr Gly Ser Ile
                245                 250                 255
Ile Ile Thr Ile Tyr Asp Ala His Thr Leu Gln Val Glu Met Pro Glu
                260                 265                 270
Ser Gly Asn Ala Pro Ser Leu Val Ala Ile Gly Arg Arg Ser Glu Ser
            275                 280                 285
Asp Cys Leu Ser Glu Glu Leu Arg His Met Asp Pro Asp Leu Gly Tyr
        290                 295                 300
Gln His Ala Leu Ser Gly Leu Ser Ser Val Lys Leu Glu Thr Val
305                 310                 315
```

<210> SEQ ID NO 6
<211> LENGTH: 3038
<212> TYPE: DNA
<213> ORGANISM: Corynebacterium glutamicum AS019
<220> FEATURE:
<221> NAME/KEY: CDS
<222> LOCATION: (115)..(1656)
<223> OTHER INFORMATION: zwf
<220> FEATURE:
<221> NAME/KEY: CDS
<222> LOCATION: (1672)..(2628)
<223> OTHER INFORMATION: opcA

<400> SEQUENCE: 6

```
cctgaagtag aatcagcacg ctgcatcagt aacggcgaca tgaaatcgaa ttagttcgat      60
cttatgtggc cgttacacat cttttcatta agaaaggatc gtgacactac catc gtg       117
                                                              Met
                                                               1 agc aca aac acg acc ccc tcc agc tgg aca aac cca ctg cgc gac ccg       165
Ser Thr Asn Thr Thr Pro Ser Ser Trp Thr Asn Pro Leu Arg Asp Pro
         5                  10                  15 cag gat aaa cga ctc ccc cgc atc gct ggc cct tcc ggc atg gtg atc       213
Gln Asp Lys Arg Leu Pro Arg Ile Ala Gly Pro Ser Gly Met Val Ile
     20                  25                  30 ttc ggt gtc act ggc gac ttg gct cga aag aag ctg ctc ccc gcc att       261
Phe Gly Val Thr Gly Asp Leu Ala Arg Lys Lys Leu Leu Pro Ala Ile
 35                  40                  45 tat gat cta gca aac cgc gga ttg ctg ccc cca gga ttc tcg ttg gta       309
Tyr Asp Leu Ala Asn Arg Gly Leu Leu Pro Pro Gly Phe Ser Leu Val
 50                  55                  60                  65 ggt tac ggc cgc cgc gaa tgg tcc aaa gaa gac ttt gaa aaa tac gta       357
Gly Tyr Gly Arg Arg Glu Trp Ser Lys Glu Asp Phe Glu Lys Tyr Val
                 70                  75                  80 cgc gat gcc gca agt gct ggt gct cgt acg gaa ttc cgt gaa aat gtt       405
Arg Asp Ala Ala Ser Ala Gly Ala Arg Thr Glu Phe Arg Glu Asn Val
             85                  90                  95 tgg gag cgc ctc gcc gag ggt atg gaa ttt gtt cgc ggc aac ttt gat       453
```

-continued

| | | |
|---|---|---|
| Trp Glu Arg Leu Ala Glu Gly Met Glu Phe Val Arg Gly Asn Phe Asp<br>100 105 110 | | |
| gat gat gca gct ttc gac aac ctc gct gca aca ctc aag cgc atc gac<br>Asp Asp Ala Ala Phe Asp Asn Leu Ala Ala Thr Leu Lys Arg Ile Asp<br>115 120 125 | 501 | |
| aaa acc cgc ggc acc gcc ggc aac tgg gct tac tac ctg tcc att cca<br>Lys Thr Arg Gly Thr Ala Gly Asn Trp Ala Tyr Tyr Leu Ser Ile Pro<br>130 135 140 145 | 549 | |
| cca gat tcc ttc aca gcg gtc tgc cac cag ctg gag cgt tcc ggc atg<br>Pro Asp Ser Phe Thr Ala Val Cys His Gln Leu Glu Arg Ser Gly Met<br>150 155 160 | 597 | |
| gct gaa tcc acc gaa gaa gca tgg cgc cgt gtg atc atc gag aag cct<br>Ala Glu Ser Thr Glu Glu Ala Trp Arg Arg Val Ile Ile Glu Lys Pro<br>165 170 175 | 645 | |
| ttc ggc cac aac ctc gaa tcc gca cac gag ctc aac cag ctg gtc aac<br>Phe Gly His Asn Leu Glu Ser Ala His Glu Leu Asn Gln Leu Val Asn<br>180 185 190 | 693 | |
| gca gtc ttc cca gaa tct tct gtg ttc cgc atc gac cac tat ttg ggc<br>Ala Val Phe Pro Glu Ser Ser Val Phe Arg Ile Asp His Tyr Leu Gly<br>195 200 205 | 741 | |
| aag gaa aca gtt caa aac atc ctg gct ctg cgt ttt gct aac cag ctg<br>Lys Glu Thr Val Gln Asn Ile Leu Ala Leu Arg Phe Ala Asn Gln Leu<br>210 215 220 225 | 789 | |
| ttt gag cca ctg tgg aac tcc aac tac gtt gac cac gtc cag atc acc<br>Phe Glu Pro Leu Trp Asn Ser Asn Tyr Val Asp His Val Gln Ile Thr<br>230 235 240 | 837 | |
| atg gct gaa gat att ggc ttg ggt gga cgt gct ggt tac tac gac ggc<br>Met Ala Glu Asp Ile Gly Leu Gly Gly Arg Ala Gly Tyr Tyr Asp Gly<br>245 250 255 | 885 | |
| atc ggc gca ccg cgc gac gtc atc cag aac cac ctg atc cag ctc ttg<br>Ile Gly Ala Pro Arg Asp Val Ile Gln Asn His Leu Ile Gln Leu Leu<br>260 265 270 | 933 | |
| gct ctg gtt gcc atg gaa gaa cca att tct ttc gtg cca gcg gca cgg<br>Ala Leu Val Ala Met Glu Glu Pro Ile Ser Phe Val Pro Ala Ala Arg<br>275 280 285 | 981 | |
| cag gca gaa aag atc aag gtg ctc tct gcg aca aag ccg tgc tac cca<br>Gln Ala Glu Lys Ile Lys Val Leu Ser Ala Thr Lys Pro Cys Tyr Pro<br>290 295 300 305 | 1029 | |
| ttg gat aaa acc tcc gct cgt ggt cag tac gct gcc ggt tgg cag ggc<br>Leu Asp Lys Thr Ser Ala Arg Gly Gln Tyr Ala Ala Gly Trp Gln Gly<br>310 315 320 | 1077 | |
| tct gag tta gtc aag gga ctt cgc gaa gaa gat ggc ttc aac cct gag<br>Ser Glu Leu Val Lys Gly Leu Arg Glu Glu Asp Gly Phe Asn Pro Glu<br>325 330 335 | 1125 | |
| tcc acc act gag act ttt gcg gct tgt acc tta gag atc acg tct cgt<br>Ser Thr Thr Glu Thr Phe Ala Ala Cys Thr Leu Glu Ile Thr Ser Arg<br>340 345 350 | 1173 | |
| cgc tgg gct ggt gtg ccg ttc tac ctg cgc acc ggt aag cgt ctt ggt<br>Arg Trp Ala Gly Val Pro Phe Tyr Leu Arg Thr Gly Lys Arg Leu Gly<br>355 360 365 | 1221 | |
| cgc cgt gtt act gag att gcc gtg gtg ttt aaa gac gca cca cac cag<br>Arg Arg Val Thr Glu Ile Ala Val Val Phe Lys Asp Ala Pro His Gln<br>370 375 380 385 | 1269 | |
| cct ttc gac ggc gac atg act gta tcc ctt ggc caa aac gcc atc gtg<br>Pro Phe Asp Gly Asp Met Thr Val Ser Leu Gly Gln Asn Ala Ile Val<br>390 395 400 | 1317 | |
| att cgc gtg cag cct gat gaa ggt gtg ctc atc cgc ttc ggt tcc aag<br>Ile Arg Val Gln Pro Asp Glu Gly Val Leu Ile Arg Phe Gly Ser Lys<br>405 410 415 | 1365 | |

-continued

| | | |
|---|---|---|
| gtt cca ggt tct gcc atg gaa gtc cgt gac gtc aac atg gac ttc tcc<br>Val Pro Gly Ser Ala Met Glu Val Arg Asp Val Asn Met Asp Phe Ser<br>420                             425                        430 | 1413 | |
| tac tca gaa tcc ttc act gaa gaa tca cct gaa gca tac gag cgc ctc<br>Tyr Ser Glu Ser Phe Thr Glu Glu Ser Pro Glu Ala Tyr Glu Arg Leu<br>435                            440                            445 | 1461 | |
| att ttg gat gcg ctg tta gat gaa tcc agc ctc ttc cct acc aac gag<br>Ile Leu Asp Ala Leu Leu Asp Glu Ser Ser Leu Phe Pro Thr Asn Glu<br>450                           455                          460                        465 | 1509 | |
| gaa gtg gaa ctg agc tgg aag att ctg gat cca att ctt gaa gca tgg<br>Glu Val Glu Leu Ser Trp Lys Ile Leu Asp Pro Ile Leu Glu Ala Trp<br>                              470                          475                        480 | 1557 | |
| gat gcc gat gga gaa cca gag gat tac cca gcg ggt acg tgg ggt cca<br>Asp Ala Asp Gly Glu Pro Glu Asp Tyr Pro Ala Gly Thr Trp Gly Pro<br>                           485                          490                        495 | 1605 | |
| aag agc gct gat gaa atg ctt tcc cgc aac ggt cac acc tgg cgc agg<br>Lys Ser Ala Asp Glu Met Leu Ser Arg Asn Gly His Thr Trp Arg Arg<br>500                           505                        510 | 1653 | |
| cca taa tttaggggca aa atg atc ttt gaa ctt ccg gat acc acc acc cag<br>Pro                     Met Ile Phe Glu Leu Pro Asp Thr Thr Thr Gln<br>                                     515                        520                        525 | 1704 | |
| caa att tcc aag acc cta act cga ctg cgt gaa tcg ggc acc cag gtc<br>Gln Ile Ser Lys Thr Leu Thr Arg Leu Arg Glu Ser Gly Thr Gln Val<br>                              530                          535                        540 | 1752 | |
| acc acc ggc cga gtg ctc acc ctc atc gtg gtc act gac tcc gaa agc<br>Thr Thr Gly Arg Val Leu Thr Leu Ile Val Val Thr Asp Ser Glu Ser<br>                           545                          550                        555 | 1800 | |
| gat gtc gct gca gtt acc gag tcc acc aat gaa gcc tcg cgc gag cac<br>Asp Val Ala Ala Val Thr Glu Ser Thr Asn Glu Ala Ser Arg Glu His<br>                           560                          565                        570 | 1848 | |
| cca tct cgc gtg atc att ttg gtg gtt ggc gat aaa act gca gaa aac<br>Pro Ser Arg Val Ile Ile Leu Val Val Gly Asp Lys Thr Ala Glu Asn<br>575                           580                        585 | 1896 | |
| aaa gtt gac gca gaa gtc cgt atc ggt ggc gac gct ggt gct tcc gag<br>Lys Val Asp Ala Glu Val Arg Ile Gly Gly Asp Ala Gly Ala Ser Glu<br>590                           595                        600                        605 | 1944 | |
| atg atc atc atg cat ctc aac gga cct gtc gct gac aag ctc cag tat<br>Met Ile Ile Met His Leu Asn Gly Pro Val Ala Asp Lys Leu Gln Tyr<br>                           610                          615                        620 | 1992 | |
| gtc gtc aca cca ctg ttg ctt cct gac acc ccc atc gtt gct tgg tgg<br>Val Val Thr Pro Leu Leu Leu Pro Asp Thr Pro Ile Val Ala Trp Trp<br>                           625                          630                        635 | 2040 | |
| cca ggt gaa tca cca aag aat cct tcc cag gac cca att gga cgc atc<br>Pro Gly Glu Ser Pro Lys Asn Pro Ser Gln Asp Pro Ile Gly Arg Ile<br>                           640                          645                        650 | 2088 | |
| gca caa cga cgc atc act gat gct ttg tac gac cgt gat gac gca cta<br>Ala Gln Arg Arg Ile Thr Asp Ala Leu Tyr Asp Arg Asp Asp Ala Leu<br>655                           660                        665 | 2136 | |
| gaa gat cgt gtt gag aac tat cac cca ggt gat acc gac atg acg tgg<br>Glu Asp Arg Val Glu Asn Tyr His Pro Gly Asp Thr Asp Met Thr Trp<br>670                           675                        680                        685 | 2184 | |
| gcg cgc ctt acc cag tgg cgg gga ctt gtt gcc tcc tca ttg gat cac<br>Ala Arg Leu Thr Gln Trp Arg Gly Leu Val Ala Ser Ser Leu Asp His<br>                           690                          695                        700 | 2232 | |
| cca cca cac agc gaa atc act tcc gtg agg ctg acc ggt gca agc ggc<br>Pro Pro His Ser Glu Ile Thr Ser Val Arg Leu Thr Gly Ala Ser Gly<br>                           705                          710                        715 | 2280 | |
| agt acc tcg gtg gat ttg gct gca ggc tgg ttg gcg cgg agg ctg aaa<br>Ser Thr Ser Val Asp Leu Ala Ala Gly Trp Leu Ala Arg Arg Leu Lys<br>                           720                          725                        730 | 2328 | |

-continued

```
gtg cct gtg atc cgc gag gtg aca gat gct ccc acc gtg cca acc gat    2376
Val Pro Val Ile Arg Glu Val Thr Asp Ala Pro Thr Val Pro Thr Asp
    735                 740                 745 gag ttt ggt act cca ctg ctg gct atc cag cgc ctg gag atc gtt cgc    2424
Glu Phe Gly Thr Pro Leu Leu Ala Ile Gln Arg Leu Glu Ile Val Arg
750                 755                 760                 765 acc acc ggc tcg atc atc atc acc atc tat gac gct cat acc ctt cag    2472
Thr Thr Gly Ser Ile Ile Ile Thr Ile Tyr Asp Ala His Thr Leu Gln
                770                 775                 780 gta gag atg ccg gaa tcc ggc aat gcc cca tcg ctg gtg gct att ggt    2520
Val Glu Met Pro Glu Ser Gly Asn Ala Pro Ser Leu Val Ala Ile Gly
            785                 790                 795 cgt cga agt gag tcc gac tgc ttg tct gag gag ctt cgc cac atg gat    2568
Arg Arg Ser Glu Ser Asp Cys Leu Ser Glu Glu Leu Arg His Met Asp
        800                 805                 810 cca gat ttg ggc tac cag cac gca cta tcc ggc ttg tcc agc gtc aag    2616
Pro Asp Leu Gly Tyr Gln His Ala Leu Ser Gly Leu Ser Ser Val Lys
    815                 820                 825 ctg gaa acc gtc taaggagaaa tacaacacta tggttgatgt agtacgcgca        2668
Leu Glu Thr Val
830 cgcatactga agatttggtt gcacaggctg cctccaaatt cattgaggtt gttgaagcag   2728 caactgccaa taatggcacc gcacaggtag tgctcaccgg tggtggcgcc ggcatcaagt   2788 tgctggaaaa gctcagcgtt gatgcggctg accttgcctg ggatcgcatt catgtgttct   2848 tcggcgatga gcgcaatgtc cctgtcagtg attctgagtc caatgagggc caggctcgtg   2908 aggcactgtt gtccaaggtt tctatccctg aagccaacat tcacggatat ggtctcggcg   2968 acgtagatct tgcagaggca gcccgcgctt acgaagctgt gttggatgaa ttcgcaccaa   3028 acggctttga                                                         3038
```

<210> SEQ ID NO 7
<211> LENGTH: 514
<212> TYPE: PRT
<213> ORGANISM: Corynebacterium glutamicum
<220> FEATURE:
<223> OTHER INFORMATION: AS019

<400> SEQUENCE: 7

```
Met Ser Thr Asn Thr Thr Pro Ser Ser Trp Thr Asn Pro Leu Arg Asp
  1               5                  10                  15

Pro Gln Asp Lys Arg Leu Pro Arg Ile Ala Gly Pro Ser Gly Met Val
             20                  25                  30

Ile Phe Gly Val Thr Gly Asp Leu Ala Arg Lys Lys Leu Leu Pro Ala
         35                  40                  45

Ile Tyr Asp Leu Ala Asn Arg Gly Leu Leu Pro Pro Gly Phe Ser Leu
     50                  55                  60

Val Gly Tyr Gly Arg Arg Glu Trp Ser Lys Glu Asp Phe Glu Lys Tyr
 65                  70                  75                  80

Val Arg Asp Ala Ala Ser Ala Gly Ala Arg Thr Glu Phe Arg Glu Asn
                 85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140
```

```
Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
            165                 170                 175

Pro Phe Gly His Asn Leu Glu Ser Ala His Glu Leu Asn Gln Leu Val
        180                 185                 190

Asn Ala Val Phe Pro Glu Ser Ser Val Phe Arg Ile Asp His Tyr Leu
    195                 200                 205

Gly Lys Glu Thr Val Gln Asn Ile Leu Ala Leu Arg Phe Ala Asn Gln
210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Pro Arg Asp Val Ile Gln Asn His Leu Ile Gln Leu
            260                 265                 270

Leu Ala Leu Val Ala Met Glu Glu Pro Ile Ser Phe Val Pro Ala Ala
        275                 280                 285

Arg Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
        435                 440                 445

Leu Ile Leu Asp Ala Leu Leu Asp Glu Ser Ser Leu Phe Pro Thr Asn
    450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
            500                 505                 510

Arg Pro

<210> SEQ ID NO 8
<211> LENGTH: 319
<212> TYPE: PRT
<213> ORGANISM: Corynebacterium glutamicum
<220> FEATURE:
<223> OTHER INFORMATION: AS019
```

<400> SEQUENCE: 8

```
Met Ile Phe Glu Leu Pro Asp Thr Thr Thr Gln Gln Ile Ser Lys Thr
  1               5                  10                  15

Leu Thr Arg Leu Arg Glu Ser Gly Thr Gln Val Thr Thr Gly Arg Val
             20                  25                  30

Leu Thr Leu Ile Val Val Thr Asp Ser Glu Ser Asp Val Ala Ala Val
         35                  40                  45

Thr Glu Ser Thr Asn Glu Ala Ser Arg Glu His Pro Ser Arg Val Ile
     50                  55                  60

Ile Leu Val Val Gly Asp Lys Thr Ala Glu Asn Lys Val Asp Ala Glu
 65                  70                  75                  80

Val Arg Ile Gly Gly Asp Ala Gly Ala Ser Glu Met Ile Ile Met His
                 85                  90                  95

Leu Asn Gly Pro Val Ala Asp Lys Leu Gln Tyr Val Val Thr Pro Leu
                100                 105                 110

Leu Leu Pro Asp Thr Pro Ile Val Ala Trp Trp Pro Gly Glu Ser Pro
            115                 120                 125

Lys Asn Pro Ser Gln Asp Pro Ile Gly Arg Ile Ala Gln Arg Arg Ile
        130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Lys Val Pro Val Ile Arg
    210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
305                 310                 315
```

<210> SEQ ID NO 9
<211> LENGTH: 960
<212> TYPE: DNA
<213> ORGANISM: Corynebacterium glutamicum
<220> FEATURE:
<223> OTHER INFORMATION: AS019
<220> FEATURE:
<221> NAME/KEY: CDS
<222> LOCATION: (1)..(957)
<223> OTHER INFORMATION: opcA

<400> SEQUENCE: 9

```
atg atc ttt gaa ctt ccg gat acc acc acc cag caa att tcc aag acc    48
Met Ile Phe Glu Leu Pro Asp Thr Thr Thr Gln Gln Ile Ser Lys Thr
  1               5                  10                  15
```

-continued

```
  1                   5                    10                     15
cta act cga ctg cgt gaa tcg ggc acc cag gtc acc acc ggc cga gtg      96
Leu Thr Arg Leu Arg Glu Ser Gly Thr Gln Val Thr Thr Gly Arg Val
            20                  25                  30 ctc acc ctc atc gtg gtc act gac tcc gaa agc gat gtc gct gca gtt     144
Leu Thr Leu Ile Val Val Thr Asp Ser Glu Ser Asp Val Ala Ala Val
        35                  40                  45 acc gag tcc acc aat gaa gcc tcg cgc gag cac cca tct cgc gtg atc     192
Thr Glu Ser Thr Asn Glu Ala Ser Arg Glu His Pro Ser Arg Val Ile
    50                  55                  60 att ttg gtg gtt ggc gat aaa act gca gaa aac aaa gtt gac gca gaa     240
Ile Leu Val Val Gly Asp Lys Thr Ala Glu Asn Lys Val Asp Ala Glu
65                  70                  75                  80 gtc cgt atc ggt ggc gac gct ggt gct tcc gag atg atc atc atg cat     288
Val Arg Ile Gly Gly Asp Ala Gly Ala Ser Glu Met Ile Ile Met His
                85                  90                  95 ctc aac gga cct gtc gct gac aag ctc cag tat gtc gtc aca cca ctg     336
Leu Asn Gly Pro Val Ala Asp Lys Leu Gln Tyr Val Val Thr Pro Leu
            100                 105                 110 ttg ctt cct gac acc ccc atc gtt gct tgg tgg cca ggt gaa tca cca     384
Leu Leu Pro Asp Thr Pro Ile Val Ala Trp Trp Pro Gly Glu Ser Pro
        115                 120                 125 aag aat cct tcc cag gac cca att gga cgc atc gca caa cga cgc atc     432
Lys Asn Pro Ser Gln Asp Pro Ile Gly Arg Ile Ala Gln Arg Arg Ile
    130                 135                 140 act gat gct ttg tac gac cgt gat gac gca cta gaa gat cgt gtt gag     480
Thr Asp Ala Leu Tyr Asp Arg Asp Asp Ala Leu Glu Asp Arg Val Glu
145                 150                 155                 160 aac tat cac cca ggt gat acc gac atg acg tgg gcg cgc ctt acc cag     528
Asn Tyr His Pro Gly Asp Thr Asp Met Thr Trp Ala Arg Leu Thr Gln
                165                 170                 175 tgg cgg gga ctt gtt gcc tcc tca ttg gat cac cca cca cac agc gaa     576
Trp Arg Gly Leu Val Ala Ser Ser Leu Asp His Pro Pro His Ser Glu
            180                 185                 190 atc act tcc gtg agg ctg acc ggt gca agc ggc agt acc tcg gtg gat     624
Ile Thr Ser Val Arg Leu Thr Gly Ala Ser Gly Ser Thr Ser Val Asp
        195                 200                 205 ttg gct gca ggc tgg ttg gcg cgg agg ctg aaa gtg cct gtg atc cgc     672
Leu Ala Ala Gly Trp Leu Ala Arg Arg Leu Lys Val Pro Val Ile Arg
    210                 215                 220 gag gtg aca gat gct ccc acc gtg cca acc gat gag ttt ggt act cca     720
Glu Val Thr Asp Ala Pro Thr Val Pro Thr Asp Glu Phe Gly Thr Pro
225                 230                 235                 240 ctg ctg gct atc cag cgc ctg gag atc gtt cgc acc acc ggc tcg atc     768
Leu Leu Ala Ile Gln Arg Leu Glu Ile Val Arg Thr Thr Gly Ser Ile
                245                 250                 255 atc atc acc atc tat gac gct cat acc ctt cag gta gag atg ccg gaa     816
Ile Ile Thr Ile Tyr Asp Ala His Thr Leu Gln Val Glu Met Pro Glu
            260                 265                 270 tcc ggc aat gcc cca tcg ctg gtg gct att ggt cgt cga agt gag tcc     864
Ser Gly Asn Ala Pro Ser Leu Val Ala Ile Gly Arg Arg Ser Glu Ser
        275                 280                 285 gac tgc ttg tct gag gag ctt cgc cac atg gat cca gat ttg ggc tac     912
Asp Cys Leu Ser Glu Glu Leu Arg His Met Asp Pro Asp Leu Gly Tyr
    290                 295                 300 cag cac gca cta tcc ggc ttg tcc agc gtc aag ctg gaa acc gtc taa     960
Gln His Ala Leu Ser Gly Leu Ser Ser Val Lys Leu Glu Thr Val
305                 310                 315
```

-continued

<210> SEQ ID NO 10
<211> LENGTH: 319
<212> TYPE: PRT
<213> ORGANISM: Corynebacterium glutamicum
<220> FEATURE:
<223> OTHER INFORMATION: AS019

<400> SEQUENCE: 10

```
Met Ile Phe Glu Leu Pro Asp Thr Thr Thr Gln Gln Ile Ser Lys Thr
  1               5                  10                  15

Leu Thr Arg Leu Arg Glu Ser Gly Thr Gln Val Thr Thr Gly Arg Val
             20                  25                  30

Leu Thr Leu Ile Val Val Thr Asp Ser Glu Ser Asp Val Ala Ala Val
         35                  40                  45

Thr Glu Ser Thr Asn Glu Ala Ser Arg Glu His Pro Ser Arg Val Ile
     50                  55                  60

Ile Leu Val Val Gly Asp Lys Thr Ala Glu Asn Lys Val Asp Ala Glu
 65                  70                  75                  80

Val Arg Ile Gly Gly Asp Ala Gly Ala Ser Glu Met Ile Ile Met His
                 85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Lys Val Pro Val Ile Arg
    210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
305                 310                 315
```

<210> SEQ ID NO 11
<211> LENGTH: 15
<212> TYPE: PRT
<213> ORGANISM: Corynebacterium glutamicum
<220> FEATURE:
<223> OTHER INFORMATION: ATCC13032
<220> FEATURE:
<221> NAME/KEY: MOD_RES
<222> LOCATION: (1)..(5)

```
<223> OTHER INFORMATION: Variable amino acid
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (10)
<223> OTHER INFORMATION: Variable amino acid

<400> SEQUENCE: 11

Xaa Xaa Xaa Xaa Xaa Pro Xaa Xaa Trp Xaa Asn Pro Leu Arg Asp
 1               5                  10                  15

<210> SEQ ID NO 12
<211> LENGTH: 15
<212> TYPE: PRT
<213> ORGANISM: Corynebacterium glutamicum
<220> FEATURE:
<223> OTHER INFORMATION: ATCC13032
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (8)..(10)
<223> OTHER INFORMATION: Variable amino acid

<400> SEQUENCE: 12

Met Ile Phe Xaa Leu Pro Asp Xaa Xaa Xaa Gln Gln Ile Ser Lys
 1               5                  10                  15

<210> SEQ ID NO 13
<211> LENGTH: 23
<212> TYPE: DNA
<213> ORGANISM: Artificial sequence
<220> FEATURE:
<223> OTHER INFORMATION: Description of artificial sequence: Primer
      zwf1

<400> SEQUENCE: 13
atygaycact ayytsggyaa rga                                            23

<210> SEQ ID NO 14
<211> LENGTH: 18
<212> TYPE: DNA
<213> ORGANISM: Artificial sequence
<220> FEATURE:
<223> OTHER INFORMATION: Description of artificial sequence: Primer
      zwf2

<400> SEQUENCE: 14
raawggmacr ccykscca                                                  18

<210> SEQ ID NO 15
<211> LENGTH: 22
<212> TYPE: DNA
<213> ORGANISM: Artificial sequence
<220> FEATURE:
<223> OTHER INFORMATION: Description of artificial sequence: Universal
      forward primer

<400> SEQUENCE: 15
gtaatacgac tcactatagg gc                                             22

<210> SEQ ID NO 16
<211> LENGTH: 19
<212> TYPE: DNA
```

<213> ORGANISM: Artificial sequence
<220> FEATURE:
<223> OTHER INFORMATION: Description of artificial sequence: M13
      forward primer

<400> SEQUENCE: 16
ggaaacagct atgaccatg                                                    19

<210> SEQ ID NO 17
<211> LENGTH: 17
<212> TYPE: DNA
<213> ORGANISM: Artificial sequence
<220> FEATURE:
<223> OTHER INFORMATION: Description of artificial sequence: Internal
      primer 1

<400> SEQUENCE: 17
tcaaccctga gtccacc                                                      17

<210> SEQ ID NO 18
<211> LENGTH: 17
<212> TYPE: DNA
<213> ORGANISM: Artificial sequence
<220> FEATURE:
<223> OTHER INFORMATION: Description of artificial sequence: Internal
      primer 2

<400> SEQUENCE: 18
ctgaccacga gcggagg                                                      17

<210> SEQ ID NO 19
<211> LENGTH: 17
<212> TYPE: DNA
<213> ORGANISM: Artificial sequence
<220> FEATURE:
<223> OTHER INFORMATION: Description of artificial sequence: Internal
      primer 3

<400> SEQUENCE: 19
atggtgatct ggacgtg                                                      17

<210> SEQ ID NO 20
<211> LENGTH: 17
<212> TYPE: DNA
<213> ORGANISM: Artificial sequence
<220> FEATURE:
<223> OTHER INFORMATION: Description of artificial sequence: Internal
      primer 4

<400> SEQUENCE: 20
ctggcgactt ggctcga                                                      17

<210> SEQ ID NO 21
<211> LENGTH: 18
<212> TYPE: DNA
<213> ORGANISM: Artificial sequence
<220> FEATURE:
<223> OTHER INFORMATION: Description of artificial sequence: Internal
      primer 5

<400> SEQUENCE: 21
cttccggata ccaccacc                                                     18

<210> SEQ ID NO 22
<211> LENGTH: 21
<212> TYPE: DNA
<213> ORGANISM: Artificial sequence -continued

```
<220> FEATURE:
<223> OTHER INFORMATION: Description of artificial sequence: zwf fwd.
      primer

<400> SEQUENCE: 22
agaatcagca cgctgcatca g                                              21

<210> SEQ ID NO 23
<211> LENGTH: 18
<212> TYPE: DNA
<213> ORGANISM: Artificial sequence
<220> FEATURE:
<223> OTHER INFORMATION: Description of artificial sequence: opcA rev.
      primer

<400> SEQUENCE: 23
agtatggtgc gcgtacta                                                  18

<210> SEQ ID NO 24
<211> LENGTH: 15
<212> TYPE: PRT
<213> ORGANISM: Brevibacterium flavum

<400> SEQUENCE: 24

Met Val Ile Phe Gly Val Thr Gly Asp Leu Ala Arg Lys Lys Leu
 1               5                  10                  15
```